(12) United States Patent  
De Mathelin et al.

(10) Patent No.: US 8,840,627 B2  
(45) Date of Patent: Sep. 23, 2014

(54) DEVICE FOR SUPPORTING AN ELONGATED BODY AND FOR THE CONTROLLED TRANSLATIONAL MOVEMENT OF THE SAME

(75) Inventors: Michel De Mathelin, Strasbourg (FR); Benjamin Maurin, Cran Gevrier (FR); Bernard Bayle, Strasbourg (FR); Jacques Gangloff, Mulhausen (FR); Olivier Piccin, Mittelhausen (FR)

(73) Assignees: Institut National des Sciences Appliquees, Strasbourg (FR); Institut de la Recherche sur les Cancers de l'Appareil Digestif (IRCAD), Strasbourg (FR); Universite de Strasbourg, Strasbourg (FR); Centre National de la Recherche Scientifique, Paris (FR)

( * ) Notice: Subject to any disclaimer, the term of this patent is extended or adjusted under 35 U.S.C. 154(b) by 1461 days.

(21) Appl. No.: 11/885,172

(22) PCT Filed: Feb. 28, 2006

(86) PCT No.: PCT/FR2006/000451  
§ 371 (c)(1),  
(2), (4) Date: Feb. 21, 2008

(87) PCT Pub. No.: WO2006/092496  
PCT Pub. Date: Sep. 8, 2006

(65) Prior Publication Data  
US 2008/0167663 A1 Jul. 10, 2008

(30) Foreign Application Priority Data

Feb. 28, 2005 (FR) ...................................... 05 02016

(51) Int. Cl.  
*A61B 19/00* (2006.01)  
*A61B 10/02* (2006.01)  
*A61B 17/34* (2006.01)  
*A61B 17/00* (2006.01)

(52) U.S. Cl.  
CPC ................. *A61B 19/20* (2013.01); *A61B 10/02* (2013.01); *A61B 19/2203* (2013.01); *A61B 2017/3409* (2013.01); *A61B 17/3403* (2013.01); *A61B 2017/00398* (2013.01)  
USPC ............................................................ 606/130

(58) Field of Classification Search  
USPC ........ 294/119.1, 106; 600/106, 114; 604/510; 606/1, 129, 130  
See application file for complete search history.

(56) References Cited

U.S. PATENT DOCUMENTS 2,744,757 A * 5/1956 Chasar .......................... 279/114  
4,765,669 A   8/1988 Meier (Continued)

FOREIGN PATENT DOCUMENTS

WO          00/28882 A    5/2000

*Primary Examiner* — Ashley Fishback  
(74) *Attorney, Agent, or Firm* — Young & Thompson

(57) ABSTRACT

A device for supporting and controlling the translational movement of an elongated body, the body extending along the longitudinal axis thereof in the form of a rod, such as a needle intended for a percutaneous medical procedure. The device is designed to be mounted to a support that can be controlled in terms of position and orientation, and includes: (i) a first member for gripping the body, whose movement can be controlled in the translation direction with a pre-determined maximum stroke; and (ii) a second fixed member which can guide the elongated body when the body is moved by the first mobile gripping member and which can maintain the body in position when the body is not engaged with the first member.

39 Claims, 17 Drawing Sheets

(56) References Cited

U.S. PATENT DOCUMENTS

| | | | |
|---|---|---|---|
| 6,665,554 B1 * | 12/2003 | Charles et al. | 600/427 |
| 6,726,675 B1 | 4/2004 | Beyar | |
| 2002/0111634 A1 * | 8/2002 | Stoianovici et al. | 606/129 |
| 2003/0171670 A1 | 9/2003 | Gumb et al. | |
| 2004/0097996 A1 * | 5/2004 | Rabiner et al. | 606/159 |

* cited by examiner

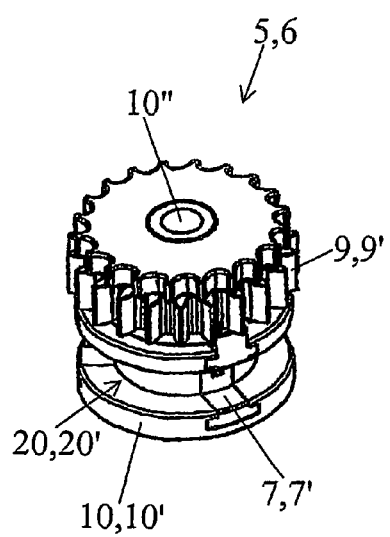
Fig. 8A
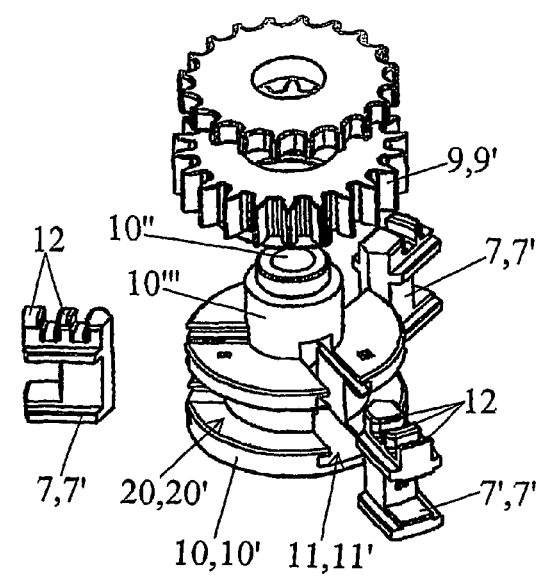
Fig. 8B
Fig. 8
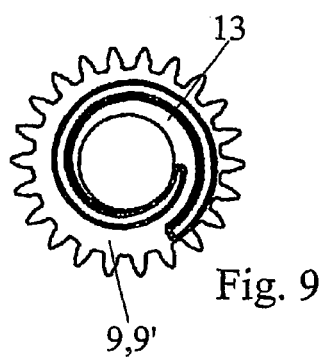
Fig. 9

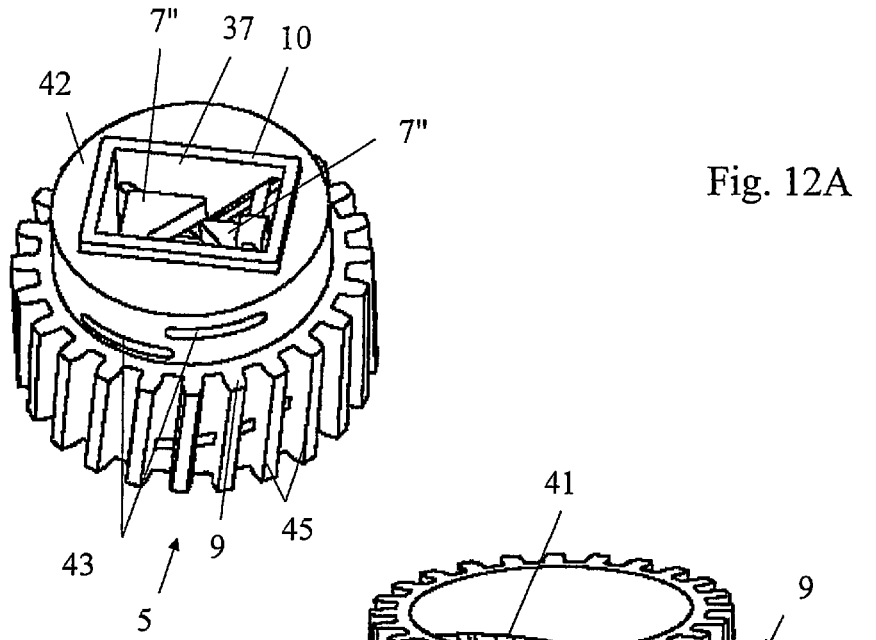
Fig. 12A
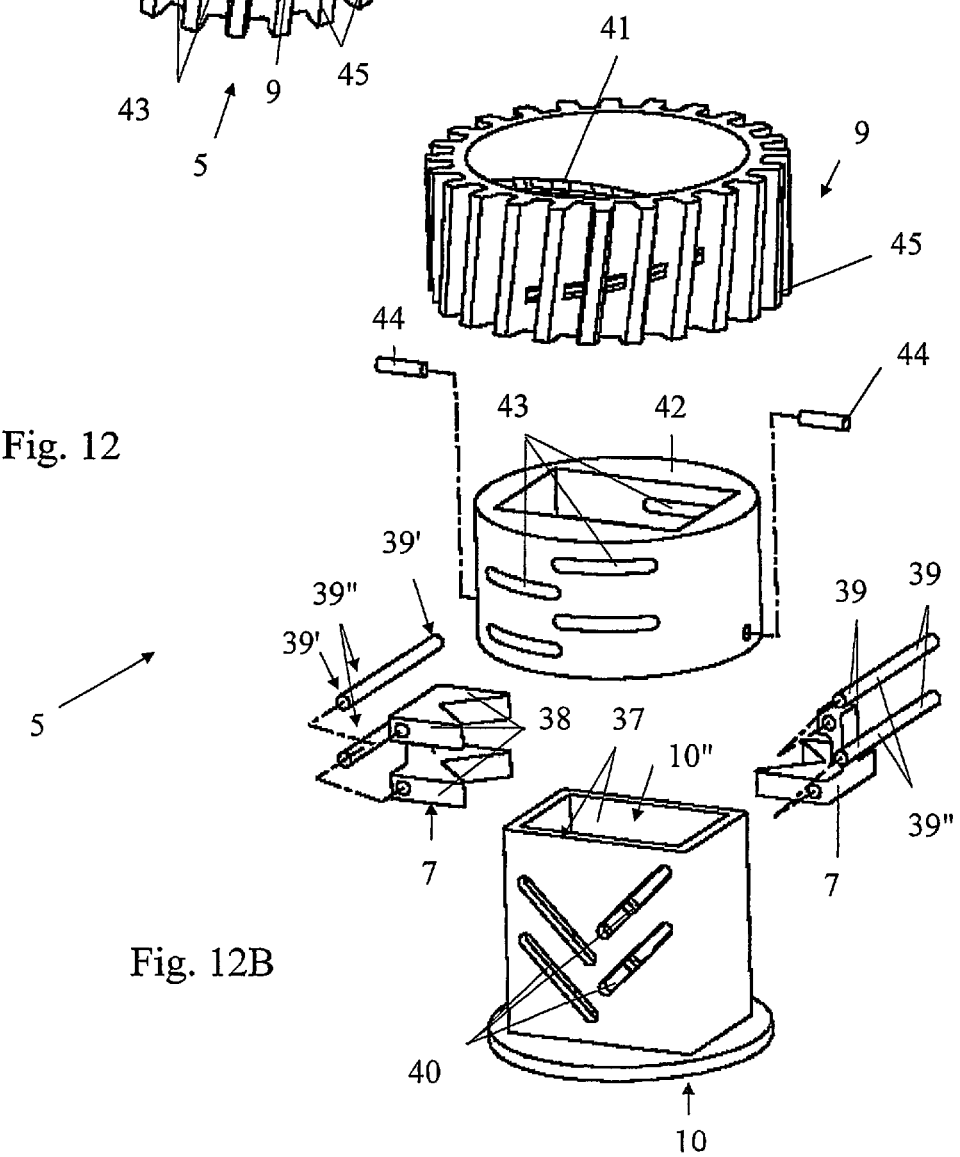
Fig. 12
Fig. 12B

DEVICE FOR SUPPORTING AN ELONGATED BODY AND FOR THE CONTROLLED TRANSLATIONAL MOVEMENT OF THE SAME

BACKGROUND OF THE INVENTION

1. Field of the Invention

This invention relates to the field of robotics, in particular in connection with the controlled movement of an object, body, piece or the like, and it has as its object a device for holding and for controlled movement of an elongated body in the form of a rod or the like.

2. Description of the Related Art

There are numerous applications in which an object, in particular elongated, is to be moved in a specific and controlled manner by a mechanical device, an electromechanical device, a mechano-pneumatic device or the like, such as a machine, device or instrument, and this in a semi-automatic manner, without direct intervention of a user or operator, though optionally under the monitoring of the latter.

Applications are known in particular in which an elongated body should be moved in translation in its longitudinal direction, for example for the purpose of driving it into another body, optionally by imitating a movement that is conventionally produced by a human operator.

Such is in particular the case for computer-assisted medical actions, for example in percutaneous procedures.

Such operating procedures are often carried out under medical imagery, in particular under CT scan, thus allowing the practitioner to monitor his procedure in real time.

However, during these procedures, the practitioner is repeatedly exposed to harmful radiation, in particular to x-rays whose intensities are further increased in fluoroscopic CAT scanning.

Now, the percutaneous medical procedures under scanner imagery are medical actions that require great precision and simultaneous protection of the patient and the surgeon, whereby these procedures consist in inserting a needle into a target organ to be treated or probed (sampling of tissues, localized injection, destruction of tumors).

There is therefore currently a need and a demand for a controlled needle insertion system.

Such a system should be both accurate and compact because of the low volume available in the CAT scanning or the like, between the chest or the abdomen of the patient and the inside wall of the tunnel of the device.

SUMMARY OF THE INVENTION

This invention relates more particularly, but not in a limiting way, to a device for inserting and extracting a needle that is designed to be mounted on a support that can be adjusted in position and in orientation of a robotic device for positioning and orientation, compatible with the application, ensuring the good direction of the tilt of the needle and allowing an optional rotation of the latter around its axis.

A robotized needle insertion device with pneumatic actuation in which the needle is clamped by a mobile jaw carrying out a translational movement is already known. However, the travel and the maximum pressure force available are limited and do not allow for the manipulation of a needle of great length.

Compact robotized devices for needle insertion based on frictional force, for example by using rollers or rolls that are driven in rotation and that hold the needle between them are also known. Owing to their design, these devices are compact, allow a long travel and naturally ensure a limitation of the force of insertion. However, this limitation of the force of insertion is neither accurate nor reproducible (it depends on many factors: surface conditions of the drive rollers and the needle, thickness of the needle, etc.). In addition, such entrainment by friction does not make it possible to define the specific position of the point of the needle (in particular during the insertion), neither to ensure directly the effective and instantaneous travel of the needle nor to evaluate the forces that are applied to the latter, nor to ensure reliably holding the needle in position in the inserted state (or in a stop position during insertion).

Finally, other devices for controlled driving of a needle or the like are also known that do not allow, in contrast, a rotation of the needle around its axis, or a possible quick release of the needle with a loose hold or with relative freedom, combined with a guaranteed recovery of said needle so that it can be re-tightened. In addition, at least some of these devices require needles of a particular shape.

The object of this invention is to eliminate at least some of these above-mentioned drawbacks, in particular but not in a limiting manner, within the context of the percutaneous surgical procedures.

For this purpose, this invention has as its object a device for holding and for controlled translational movement, in its longitudinal direction, of a rod-shaped elongated body, in particular of a needle, and in particular a needle for a percutaneous medical procedure, a device that is designed to be mounted on an adjustable support in a manner that is controlled in position and in orientation, such as, for example, a platform or an arm of a robotic device for positioning and orientation, whereby this device essentially comprises, on the one hand, a first part for gripping the elongated body, movable relative to the support in a manner that is commanded and/or controlled in the translational direction with a predetermined maximum travel, and, on the other hand, a second part that is stationary relative to the support and able to guide the elongated body when the latter is moved by the first movable gripping part and, if necessary, to keep said elongated body in position when the latter is not engaged with said first part, whereby the two parts are aligned in the translational direction and whereby the first part can be moved alternately between a proximal position of the second part and a distant position of the latter device, characterized in that the movable gripping part comprises clamping means, whereby the elongated body is locked, and consists of a mandrel through which the elongated body passes, whereby said mandrel can be moved in rotation with the elongated body around the translational axis.

BRIEF DESCRIPTION OF THE DRAWING FIGURES

The invention will be better understood using the description below, which relates to preferred embodiments, provided by way of nonlimiting examples and explained with reference to the accompanying diagrammatic drawings, in which:

FIGS. 1 (a) to 1 (e) are diagrammatic representations that illustrate the various operating phases of an elongated-body movement cycle that is produced using two parts of a device for holding and for controlled movement according to a first embodiment of the invention;

FIGS. 8A and 8B are perspective views, respectively in the assembled state and in the exploded state, of a first variant embodiment of a mandrel that forms the first and second parts of the device of FIGS. 2 and 3;

FIG. 9 is a detail view of the lower face of the ring that is part of the mandrel that is shown in FIGS. 8A and 8B;

FIGS. 12A and 12B are perspective views respectively in the assembled state and in the exploded state of a second variant embodiment of a mandrel in connection with other embodiments of the device according to the invention;

DETAILED DESCRIPTION OF THE INVENTION

Figure 1:
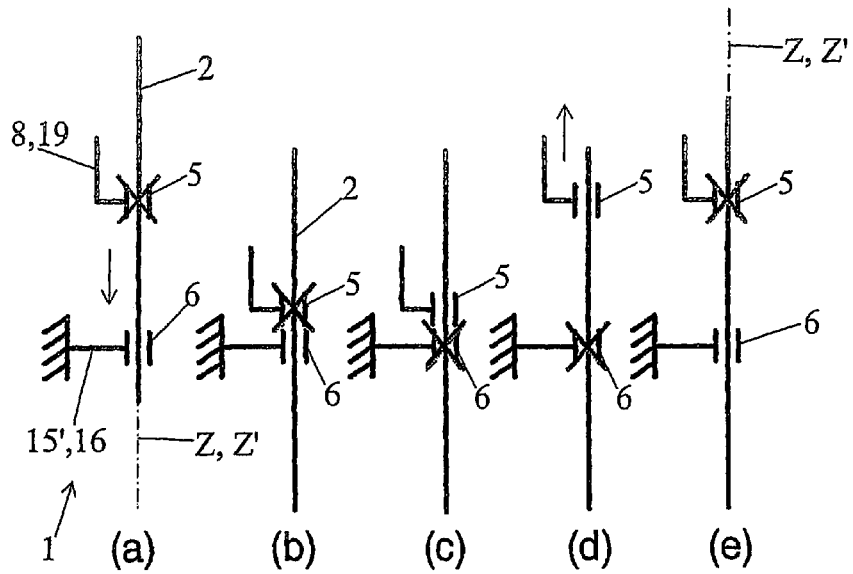

By way of example, FIGS. 2, 3, 13, 14 and 15 illustrate a device 1 for holding and for controlled translational movement of a rod-shaped elongated body 2 in its longitudinal direction Z', in particular a needle, and in particular a needle for a percutaneous medical procedure. This device 1 in particular is designed to be mounted on a support 3 that is adjustable, in an controlled manner, in position and in orientation, such as, for example, a platform or an arm 3 of a robotic device 4 for positioning and orientation.

This device 1 for holding and for controlled movement essentially comprises, on the one hand, a first part 5 for gripping the elongated body 2, movable in a controlled manner in the translational direction Z with a predetermined maximum travel, and, on the other hand, a second stationary part 6, able to guide the elongated body 2 when the latter is moved by the first movable gripping part 5, and, if necessary, able to hold said elongated body 2 in position when the latter is not engaged with said first part 5, whereby the two parts 5 and 6 are aligned in the translational direction Z and whereby the first part 5 can be moved in an alternative manner between a proximal position of the second part 6 and a distant position of the latter.

According to the invention, the movable gripping part 5 comprises clamping means 7, whereby the elongated body 2 is locked, and consists of a mandrel through which the elongated body 2 passes, whereby said mandrel 5 can be moved in rotation with the elongated body 2 around the translational axis Z.

Preferably, and as FIGS. 8, 9, 11 and 12 show it, the tightening and loosening movements of the mandrel 5 are controlled by a rotary maneuvering part 9, preferably in the form of a maneuvering ring gear or toothed maneuvering ring, integrated in said mandrel 5 and in that the jaw-shaped tightening means 7 are mounted, with the capability of guided sliding, in a body 10 with a tubular passage 10" that is designed to hold the elongated body 2 in such a way that the body surrounds said passage and said passage extends through the body, whereby the movement of said jaws 7 is generated by a rotational movement of said maneuvering ring 9 that surrounds the body 10.

By this embodiment of the gripping part 5, it is possible to ensure that after each relaxation of the tightening of the body 2 and optionally combined with a movement in translation of said part, it is possible to ensure a new hold by tightening said elongated body 2, the latter remaining in the tubular passage 10".

According to a first alternative movement of the elongated body 2, allowing an automated or assisted movement of the latter, for example monitored by a computer unit, it can be provided that the mandrel 5 that forms the moving gripping part is mounted on or in a cart 8 that can be moved by motorized driving in the two directions opposite from the translational direction Z of said elongated body 2, by being guided in an elongated support structure 15 that is able to be assembled quickly with the platform or the arm 3 of a robotic device 4 for positioning and orientation, whereby said support structure 15 is advantageously shaped so as to allow lateral access to the body 2 that is engaged in the support structure 15 and optionally an installation and an extraction at a lateral or radial slant from the body 2, if necessary with the mandrel 5 (FIGS. 2, 3, 14 and 15).

Figure 13A:
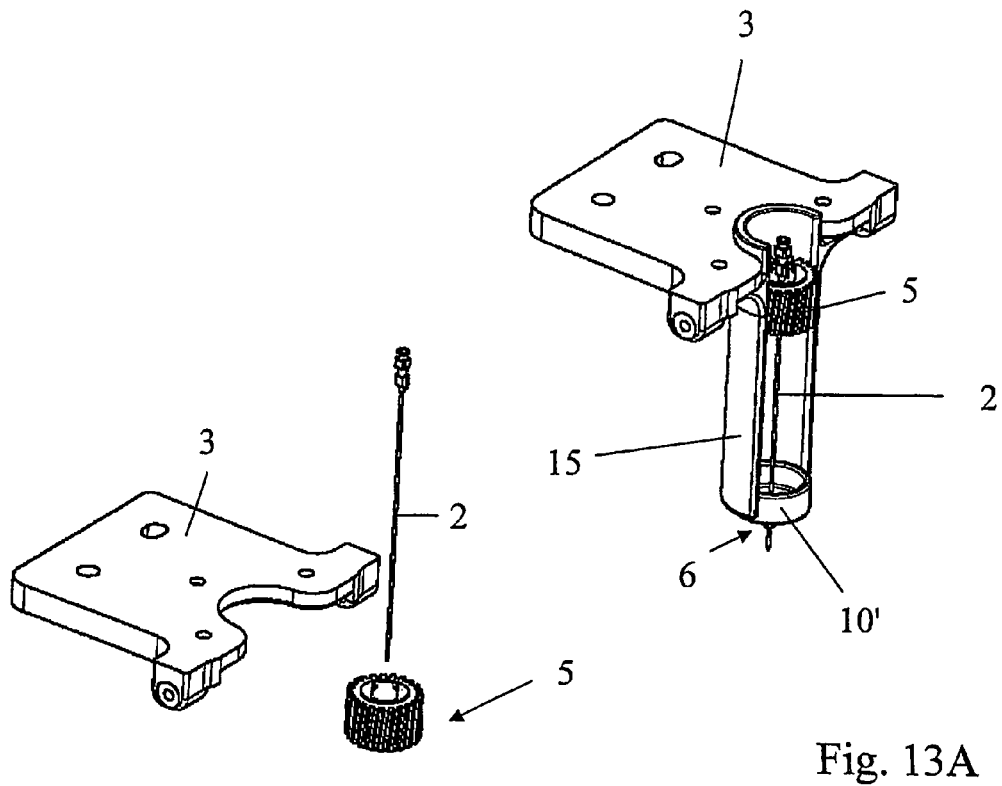
FIGS. 13A and 13B are perspective views, respectively in the assembled state and in the exploded state, of a device according to a second embodiment of the invention, in connection with a platform of a robotic positioning system.
Figure 13:
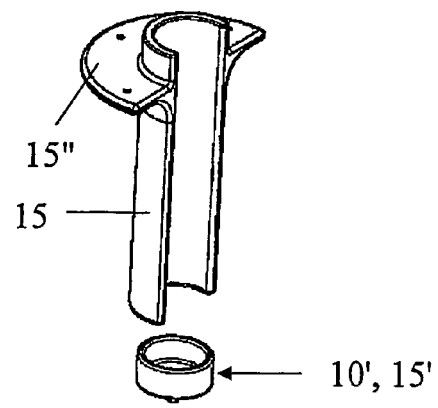
Figure 13B:

According to a second alternative movement of the elongated body 27 shown in FIGS. 13A and 13B of the accompanying drawings, the mandrel 5 that forms the moving gripping part is housed directly in a support body 15 that is elongated with the capability of guided sliding in the translational direction Z of the elongated body 2 and with the capability of rotation around said axis 2, said support body 15 that forms a slide for said moving mandrel 5, whose travel preferably results directly from the manual action of an operator, whereby said support structure 15 is advantageously shaped so as to allow lateral access to the body 2 that is engaged in the support structure 15, and optionally an installation and an extraction at a lateral or radial slant from the body 2.

In this latter case, the penetration and the retraction of the body 2 are controlled directly by a human operator, for example by a surgeon when it is a matter of a needle.

So as to allow this above-mentioned lateral access, the support structure 15, which acts as a guide support to the cart 8 or as a guide to the mandrel 5, advantageously offers a cutaway or a lateral release extending essentially over the entire length of this structure 15 in the direction Z (see preceding figures).

In the two above-mentioned travel alternatives, the mandrel 5 (optionally in cooperation with the part 6) acts as an adaptor or interface for assembly and guiding of the elongated body 2 in the support structure 15, with, in addition, a gripping function by tightening for the purpose of a driving in translation and in rotation of said body.

As FIGS. 2, 3, 14, and 15 show in particular, the second stationary part 6 is located at the end of the support body 15 with an elongated structure, which is distal relative to the platform or to the arm 3 that holds said device 1, by being a body 10' that is connected to this support body 15 or formed by a portion of the latter.

According to a first variant embodiment of the second stationary part 6, the latter can consist of an adjusted guide bearing of the elongated body 2, whereby the friction between the latter and said bearing is at least enough to ensure that said elongated body 2 is held against gravity.

The friction forces advantageously also will be enough to prevent axial travel of the elongated body 2 during the return travel phase, in the loosened state, of the moving mandrel 5 (FIGS. 1 (c) and 1 (d)).

Figure 14:
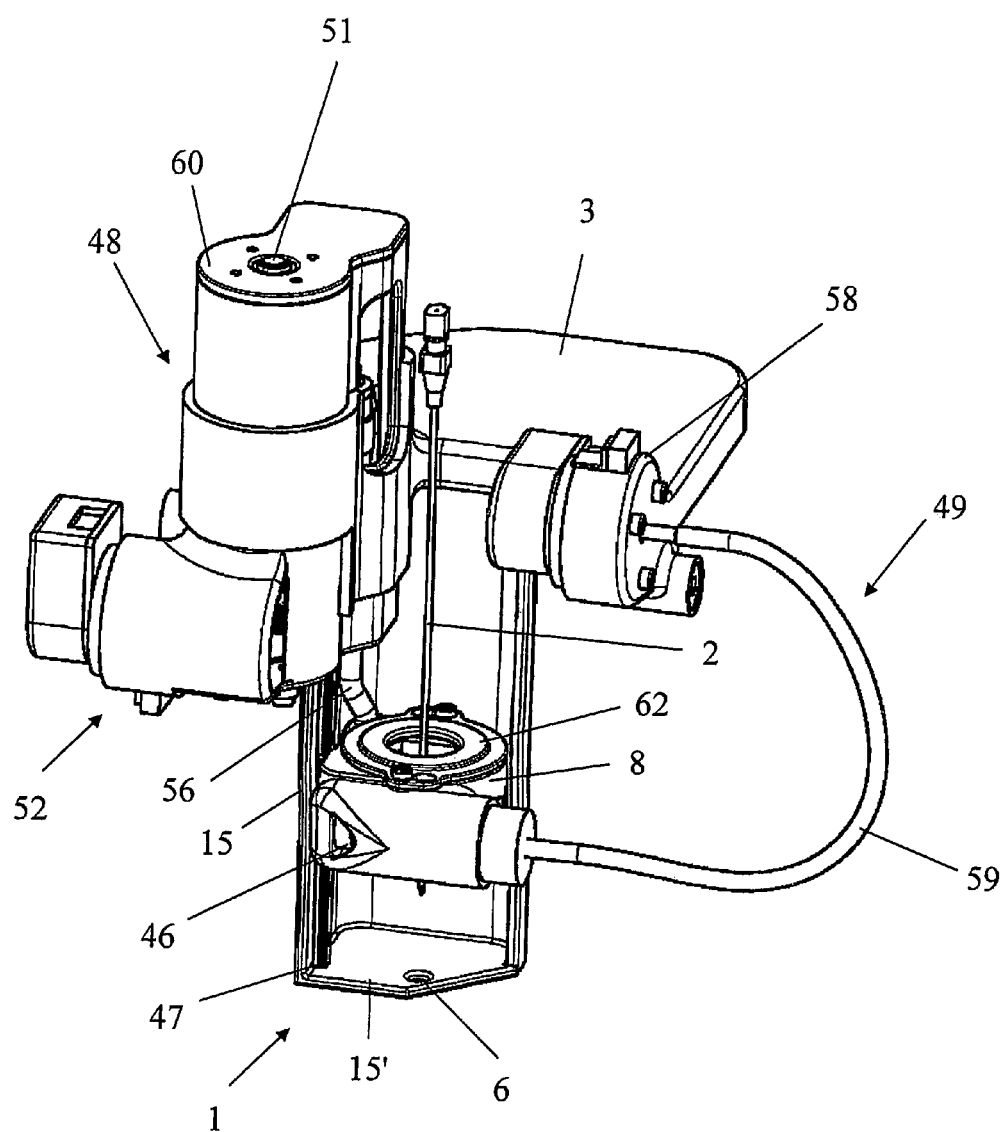
FIG. 14 is a perspective view of a device according to a third embodiment of the invention.
Figure 15:
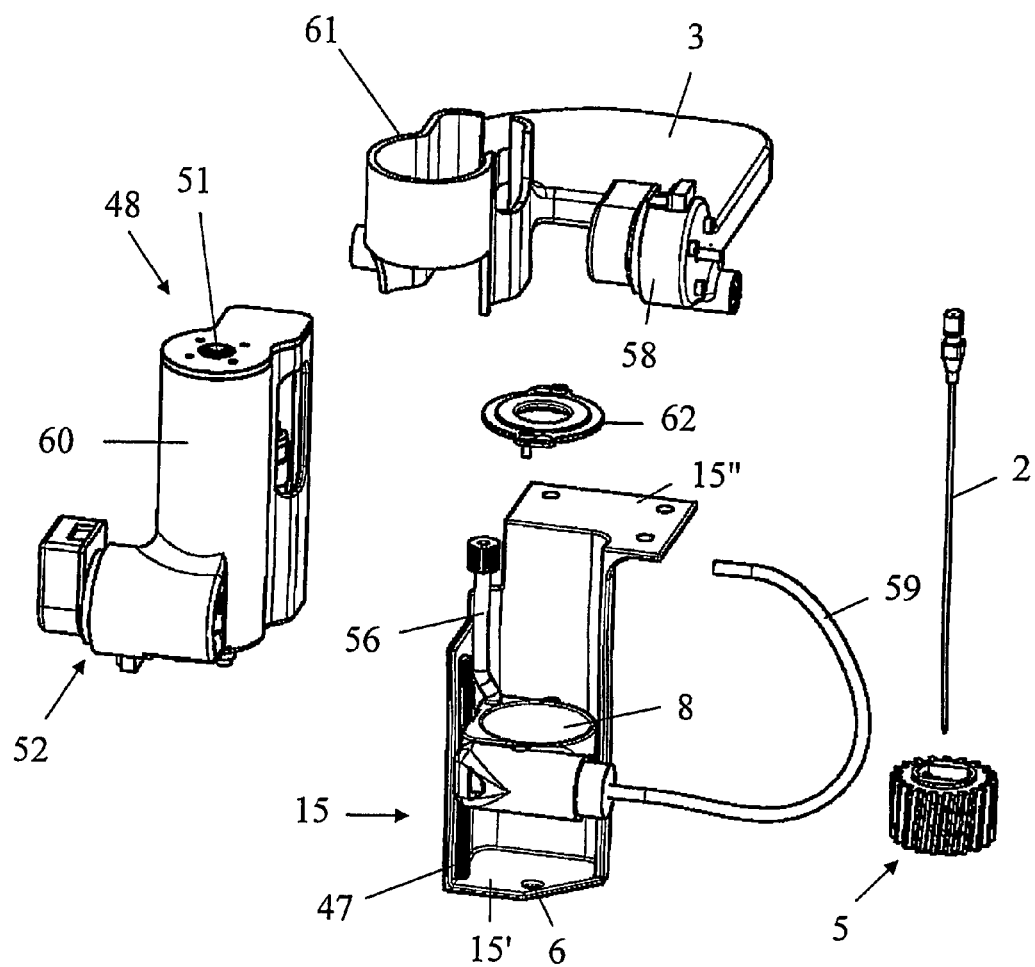
FIG. 15 is an exploded view of the device of FIG. 14.

According to a second variant embodiment of the second stationary part 6, shown in FIGS. 14 and 15 in particular, said second stationary part 6 consists of an opening or a guide channel with play of the elongated body 2, designed to limit the radial jarring or the angular slope of the elongated body 2 relative to the translational direction Z and to hold said elongated body 2 essentially in a coaxial arrangement with said direction Z, in cooperation with the mandrel 5 that forms a moving gripping and driving part.

The guide channel with play can consist of, for example, a channel that is tapered in the positive direction of the direction Z, obtained by deformation with piercing of a wall.

Figure 2:
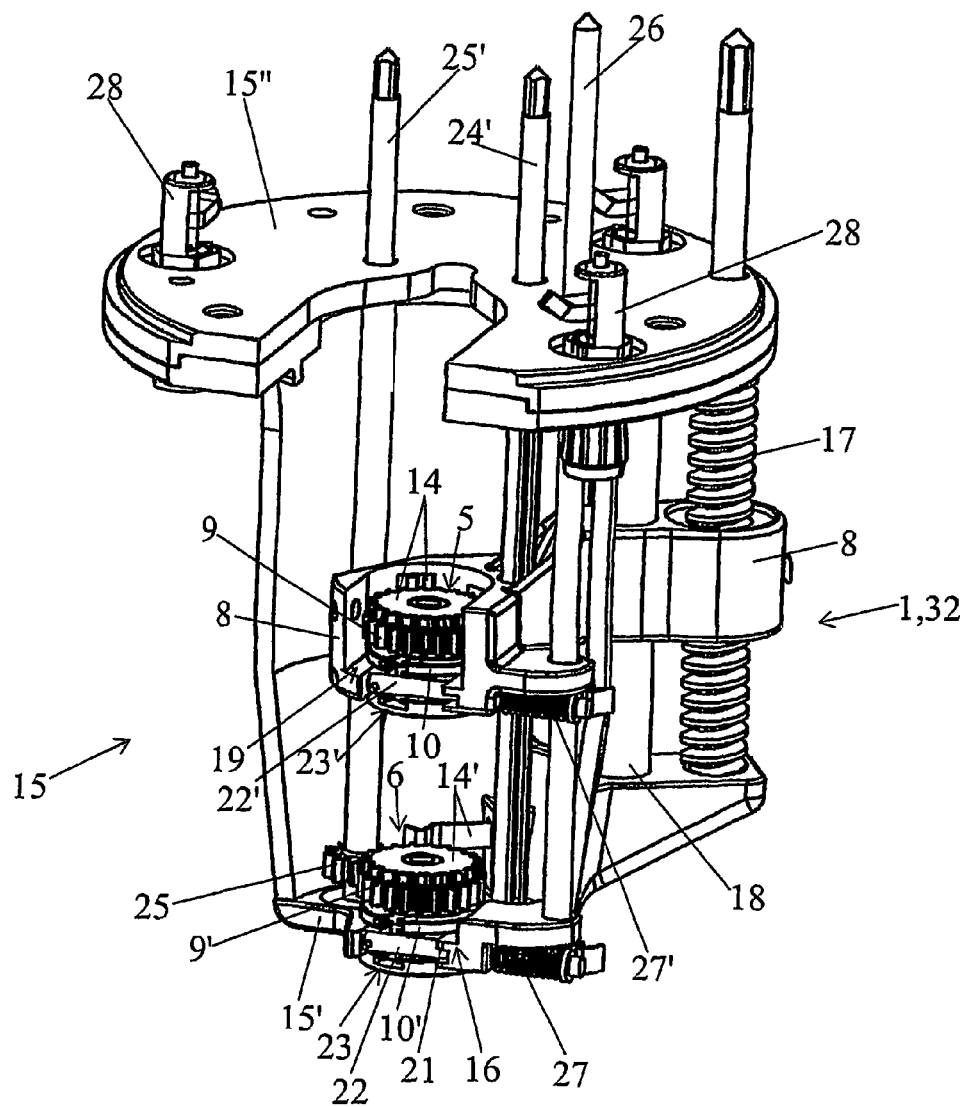
FIG. 2 is a perspective view of an embodiment of the two parts of FIG. 1 and their means of command and support that are part of the device according to a first embodiment of the invention and that form a module of the latter.
Figure 3:
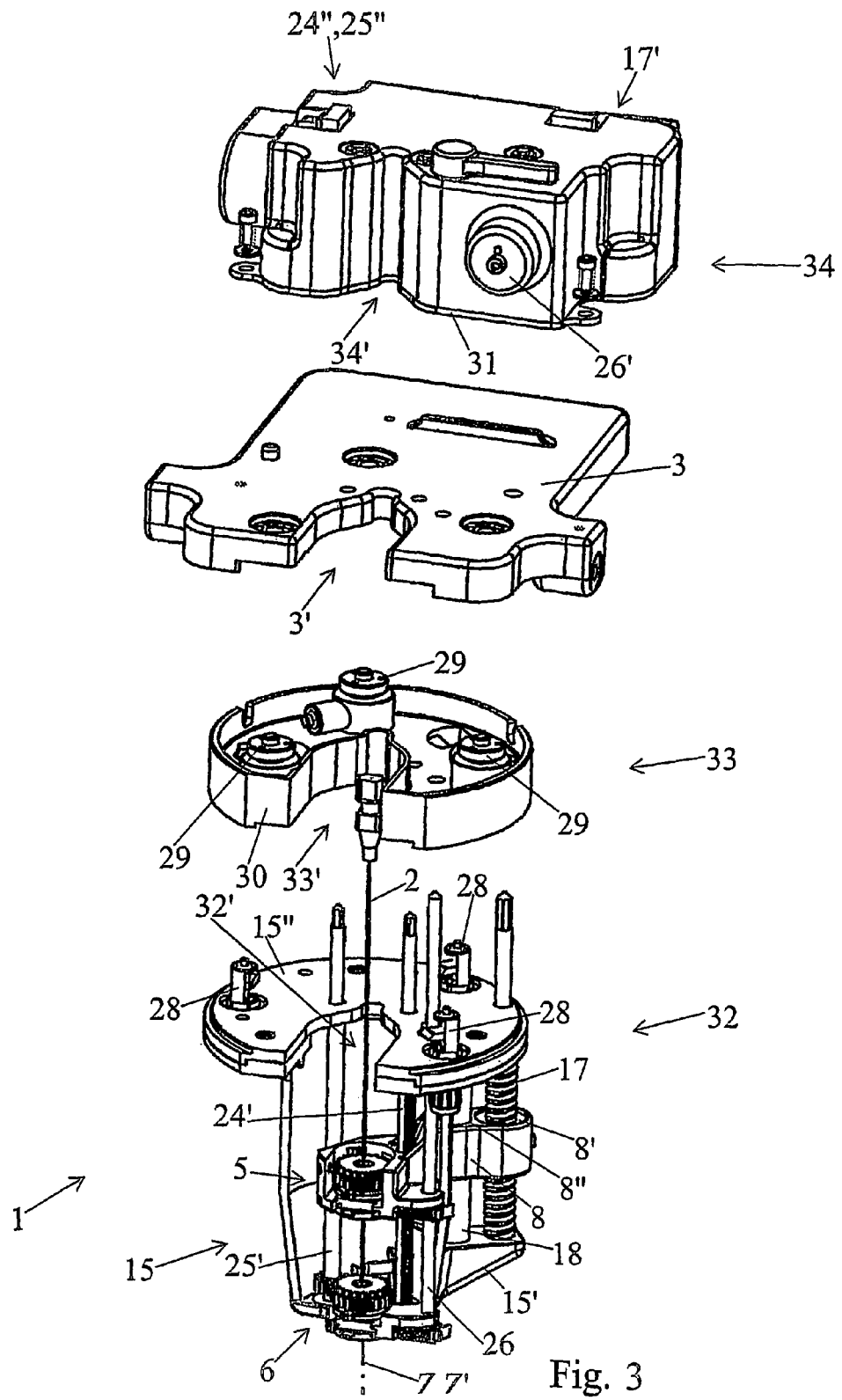
FIG. 3 is an exploded perspective view of a first embodiment of the device according to the invention, showing its different constituent modules, as well as a corresponding assembly platform of a robotic device for its operation and its orientation.

According to a third variant embodiment of the second stationary part 6, shown in FIGS. 1, 2 and 3, the second stationary part 6 performs a controlled gripping function of the elongated body 2 and consists of a mandrel through which the elongated body 2 extends, whereby this second mandrel 6 has a structure, a mode of operation and constituent elements that are identical to those of the first mandrel 5, namely in particular a maneuvering ring 9', jaws 7' and a body 10' with a tubular passage 10''.

In particular in connection with the first and third above-mentioned variants, it may be advantageous to break down the total translative motion in question into various smaller-scale displacements that are repeated cyclically, whereby the first moving part 5 successively grasps the elongated body 2 at locations distributed along the latter. FIG. 1 diagrammatically illustrates such a travel cycle (whereby the cross on the part 5 indicates that the latter has a hold on the body 2).

As is evident from FIG. 1, the two mandrels 5 and 6 are controlled by phase opposition, i.e., when one of them is tightened on the body 2, the other is loosened, and vice versa.

Thus, during the effective translation phases and when the mandrel 5 is not in an end position, it is this mandrel 5 that tightens and holds the elongated body 2. The stationary mandrel 6 is therefore tightened only during the inverse translation phases of the mandrel 5 that is not tightened.

So as to avoid the absence of any engagement on the body 2 and therefore a possible uncertainty on the position or the travel of the latter, it can be provided that the tightening phases of two mandrels 5 and 6 are at least slightly overlapping to ensure simultaneous contact of the two mandrels 5 and 6 with the body 2 at least over a short interval of time.

The use of the mandrels for the parts 5 and 6 also makes it possible to be able to manipulate, without other modification or adjustment, elongated bodies 2 of different diameters (in a range of given values, for bodies 2 of round sections), and even bodies 2 of polygonal sections.

In addition, the jaws 7, 7' can comprise teeth whose profile ensures reliable engagement and travel of the elongated body 2, in particular a locking of the body 2 in the direction of the positive movement in the tightened state of the mandrel in question (in particular the mandrel 5).

Thus, it can be provided to fractionate the total translational movement of the elongated body 2 into a sum of consecutive elementary translations.

As is evident from FIG. 1, the cart 8 is found in a top position in a first step and at the beginning of an operation and a translation phase, whereby the mandrel 5 is then tightened on the body 2, while the jaws 7' of the mandrel 6 are only just in contact with said body 2. In this way, this latter mandrel 6 insures a simple guiding in translation of the body 2.

The elementary translational movement is then broken down into four phases, as indicated below:

Drop of the cart 8 over the length of the elementary travel (FIG. 1a),

When the cart 8 reaches the low end-of-travel (FIG. 1b), the mandrel 5 is loosened, whereas the mandrel 6 is simultaneously tightened (FIGS. 1b and 1c), The cart 8 is then brought into its initial position, whereby the mandrel 5 remains loosened (FIG. 1d), When the mandrel 5 arrives in the initial position, it is tightened, whereas the mandrel 6 is loosened (FIG. 1e).

Of course, the translational movement of the body 2 in the opposition direction could be carried out by simply reversing the above-mentioned operations.

This breakdown or this fractionation of the total translational movement can also be implemented when the second stationary part 6 is produced in accordance with its second above-mentioned variant embodiment, in particular when holding the body 2 against gravity is not necessary (for example a needle 2 that is embedded in a body). In this case, the moving part 5 acts as described above in connection with FIG. 1, and the stationary part 6 ensures a relative holding (with play) of the embedded body 2.

In connection with the FIGS. 1 to 9 of the accompanying drawings, more specifically a first embodiment of the device 1 for holding and for travel is described below.

As FIGS. 8A and 8B show it and according to a possible first practical variant embodiment, the mandrel 5, 6, or each mandrel 5, 6, essentially consists of a body 10, 10' with a tubular through passage 10'', open laterally for allowing the passage of at least two, preferably three, jaws 7, 7' and provided with guide means 11, 11' of said jaws 7, 7' in a radial direction relative to the tubular passage of the parts (10, 10') in question. Said jaws 7, 7' are distributed uniformly around said passage 10'' and can be moved between a so-called tightening position in which they extend partially into the corresponding passage 10'' and a position in which they totally release said passage 10''. In addition, said jaws 7, 7' comprise rib/groove segments 12 that can be engaged and that can circulate in a groove/rib 13 in a spiral portion that is made in a lateral face of a toothed maneuvering ring gear 9, 9' that is mounted with the capability of rotation on a portion with a tubular external shape 10''' of the body 10, 10' of the mandrel in question 5, 6, a rotation of said ring 9 or 9' that entrains a simultaneous or identical radial slide of the jaws 7 or 7'.

Figure 7:
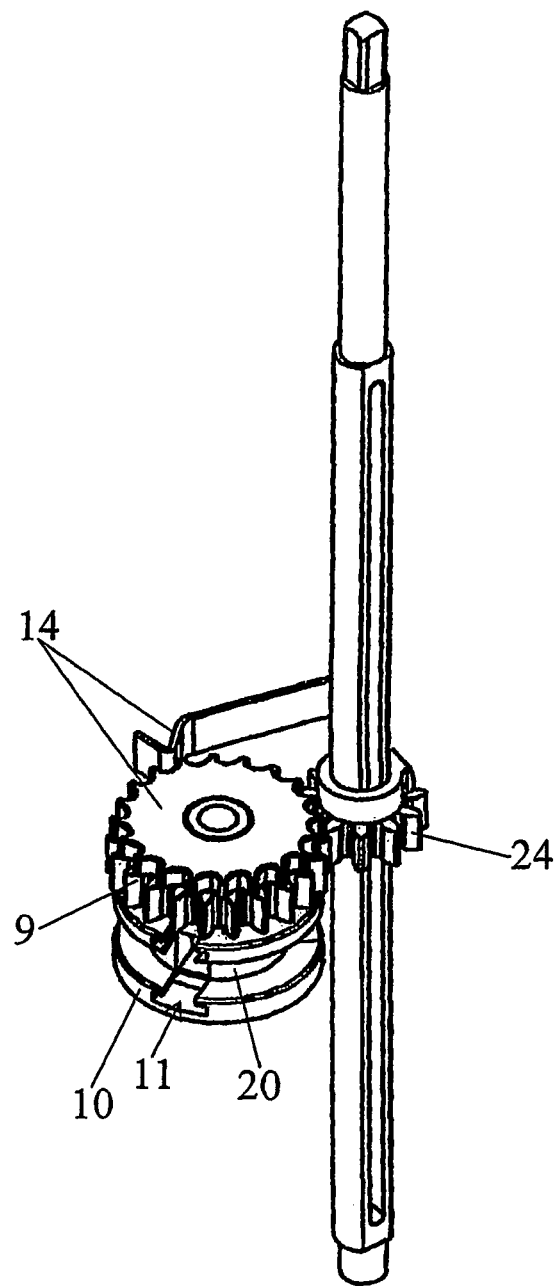
FIG. 7 is a detail view that shows the actuation of the sliding mandrel that forms the first gripping part, as shown in FIGS. 2 and 6.

According to an additional characteristic of the invention, evident from FIGS. 2 and 7 of the accompanying figures, the mandrel 5, 6 or each mandrel 5, 6 is mounted (in the cart 8 or on the site 16) with the capability of rotation around the longitudinal axis Z' of the elongated body 2 that passes through it, if necessary together with the latter, and a pawl mechanism 14, 14' that locks the body 10, 10' of said mandrel 5,6 in question against rotation in the direction of loosening and that allows a gradual rotation of said mandrel 5, 6, in the direction of tightening—when the latter is thoroughly tightened around the elongated body 2, and when an additional tightening torque, having an intensity that is greater than a determined value defined by the pawl mechanism 14, 14' in question, is applied at the corresponding toothed maneuvering ring 9, 9'—is combined with each mandrel 5, 6.

Thanks to this arrangement, it thus is possible not only to ensure a reliable loosening, but also to transmit to the elongated body 2 a controlled and progressive rotational movement (with calibration in the direction of reverse rotation) around its longitudinal axis, and this in addition to its translational movement.

As FIGS. 2, 3 and 7 also show, each of the pawl mechanisms 14, 14' can consist of, for example, a foot or a leaf spring with a segment that is folded in the shape of a tooth that is engaged in the teeth or the notches of a ring or a ring that is integral with the core 10, 10' of the mandrel in question 5, 6.

The shape of the teeth and the degree of resistance to the deformation of the leaf spring will determine the value of the additional torque to be applied to obtain a rotation of the mandrel in question.

Thus, the pawl mechanisms 14 and 14' make it possible to lock the rotation of the mandrels 5 and 6 respectively in one direction. This property is useful during the loosening of said mandrels to prevent the rotation of the corresponding mandrel body 10, 10' during the actuation of the ring 9, 9' in question. In terms of tightening, these pawl mechanisms 14, 14' make it possible for mandrels 5 and 6 to turn on themselves beyond a certain tightening threshold of the elongated body 2, thus allowing a rotation of said body 2 around its axis Z'.

As FIGS. 2 and 3 also show, the first moving part 5 and the second stationary part 6 are mounted, preferably in a removable manner, on a support structure 15 that can be assembled rigidly with the platform or the arm 3 of a robotic device 4 for positioning and orientation, whereby the support structure 15 in the form of a chassis has a given extension in the translational directional movement Z of the elongated body 2, comprising a mounting site 16 for the second stationary part 6, positioned at the extreme end in the direction corresponding to a positive movement or embedding of said elongated body 2 in the translational direction Z, and being equipped with means 17, 18 for guiding and controlled movement of the first moving part 5 that is mounted, at a suitable corresponding mounting site 19, on or in a cart 8 that works with these means 17, 18.

Consistent with an advantageous embodiment of the invention, the means for guiding and controlled movement of the first moving part 6 comprise, on the one hand, a threaded shaft 17 that forms a mother screw, and, on the other hand, at least one guide rail or rod 18. In addition, the cart 8 integrates a threaded perforation 8' that forms a nut and at least one bearing or guide shoe 8" that may or may not pass through and that works, in a sliding manner, with the guide rail or rod 18 or each guide rail or rod 18.

Preferably, the first and second parts 5 and 6 that come in the form of mandrels are accommodated in a removable manner and with the capability of rotation in their respective essentially U-shaped mounting sites 16 and 19. In addition, the bodies 10, 10' of the mandrels 5, 6 that are generally circular-cylindrical in shape have an outside circumferential groove 20, 20', and the mounting sites 16 and 19 each have a rib 21, 21' that can work with the groove 20, 20' of the corresponding body 10, 10' of mandrel 5, 6, over a portion of their circumferential extension, for the purpose of the retention of said body 10, 10'. Finally, said mounting sites 16, 19 are open laterally to allow the installation and removal of said mandrels, 5, 6, whereby the latter are locked in the mounted state in their respective sites 16, 19 by moving locking pieces 22, 22', preferably stressed elastically in the locking position of said mandrels 5, 6, whereby these locking pieces 22, 22' become engaged in the outside grooves 20, 20' of the body 10, 10' of the mandrels 5, 6 respectively in question in the continuity of the ribs 21, 21' and by closing the lateral openings 23, 23' of the respective mounting sites 16, 19.

In some applications, in particular medical applications, it may be necessary to use a possibility of release or quick and optionally automatic disengagement of the elongated body with the device 1.

For this purpose, the first and second parts 5 and 6 can be mounted in their mounting sites 19 and 16 respectively against an elastic stressing, whereby the latter ejects said parts 5 and 6 beyond said sites 19 and 16 when the locking pieces 22, 22', preferably controlled simultaneously, release the corresponding lateral openings 23 and 23'.

This elastic stressing can be provided by, for example, a leaf spring that is deformed by the installation of the mandrel.

Alternatively, it may also be provided that the cart 8 that holds the gripping part 5 is connected in a removable manner to said device 1 by being able in particular to be moved into an end sliding position in which it becomes disengaged from said device 1.

In the two above-cited variants, the disengagement is carried out between the device 1 and the parts 5 and 6, whereby the latter remain connected to the body 2.

So as to allow in particular an offset of the actuation means of the mandrels 5 and 6, while ensuring a reliable and robust control, the driving of the maneuvering ring 9, 9' of each part in the form of a mandrel 5, 6 can be carried out via a gear 24, 25 that engages with said ring 9, 9' and is integral in rotation with a rod or a shaft 24', 25' that is driven in rotation by a corresponding, optionally common, respective actuator 24", 25". The gear 25 that engages with the ring 9' of the fixed mandrel 6 is made integral rigidly at the end of a corresponding drive shaft 25' and wherein the gear 24 that engages with the ring 9 of the moving mandrel 5 is integral in rotation and free in translation relative to a corresponding drive shaft 24' (FIG. 7).

In addition, the device 1 can also comprise a pivoting or sliding control rod or pole 26 that is connected in driving with the locking rods 22, 22' for the purpose of their travel beyond their locking position against elastic stressing forces, for example provided by compression springs 27, 27', whereby this control rod 26 is integral in driving an actuating mechanism 26', in particular a safety mechanism that causes unlocking by default.

The actuating mechanism 26' can consist of, for example, an electromagnetic suction cup that keeps a locking blade armed that is returned by a spring and is integral with the control rod 26. In the absence of the current, the holding action of the suction cup disappears and the locking blade pivots by one turn fraction by driving the control rod 26. The latter then entrains the movement of locking pieces 22 and 22' and consequently the release of mandrels 5 and 6.

It should be noted that one or more of the above-mentioned rods 24', 25' and 26 optionally can act as an additional guide rod for the cart 8, at least to ensure non-restrictive guiding (with no interference with the rotational movement of the rod in question).

When the device 1 is used in an environment and in connection with the sterile material, it can be provided that the shafts 24' and 25' as well as the control rod 26 have free ends, on the side of the actuators 24", 25", respectively of the mechanism 26', tapered or pointed, in particular able to pierce the wall of a sterile package.

In the actual example illustrated in FIGS. 2 and 3 in particular and still in connection with the first embodiment of the device 1, the chassis that forms a support structure 15 comprises a lower plate 15' that contains the mounting site at the extreme end 16 for the second part 6 and an upper plate 15" for attachment to the platform 3 of a robotic device 4 for operation and orientation, whereby said upper plate 15" is equipped with quick assembly means 28, such as, for example, latches, able to become engaged with said platform 3 or with a piece that is integral with the latter in the mounted state of said chassis 15. The means 17, 18 for guiding and controlled movement, as well as, if necessary, the drive shafts 24', 25' and the control rod 26, extend and are mounted between these two plates 15' and 15", whose mutual spacing essentially determines the travel of the first moving part 5.

The lower plate 15 will comprise bearings for the control rods 24', 25', 26 and the shaft 17, whereby the upper plate 15" comprises through openings, optionally also forming bearings.

The two plates 15' and 15" can be connected by, for example, crosspieces or one or more wall portions, whereby these last elements optionally can provide rails or additional guide rods for the cart 8.

So as to use information on the movement of the body 2 in addition to its position and to be able, if necessary, to install safety measures, the device can comprise one or more force sensors 29, 54' that measure the intensity of the thrust exerted on the elongated body 2 in the translational direction Z, and, if necessary, the torque or certain components at least of the torque that is exerted on this elongated body 2.

According to an advantageous method for construction and mounting of the device 1, said force sensors 29 are arranged between the upper plate 15" of the support structure 15 and the platform 3 of the robotic device 4 and are preferably mounted on a separator 30 that is sandwiched between said upper plate 15" and said platform 3.

In this embodiment and to ensure a complete transmission of the forces/stresses that are exerted on the body 2 with sensors 29, the latches 28 become engaged on or in the plate 30, whereby the latter is fixed on the platform 3.

Figure 4A:
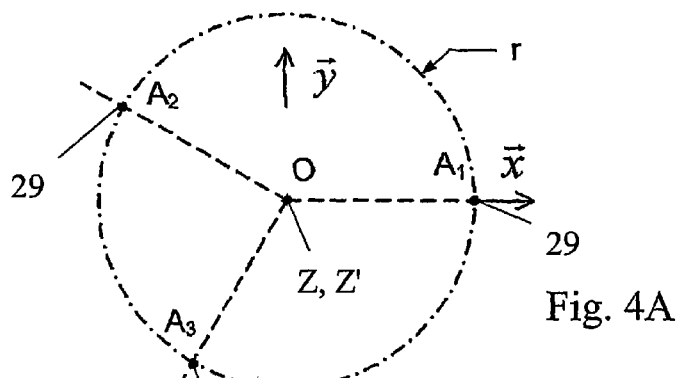
FIGS. 4A and 4B are respectively top and lateral elevation diagrammatic representations that show the arrangement of the sensors of forces or stresses that are part of the device according to the invention.
Figure 4B:
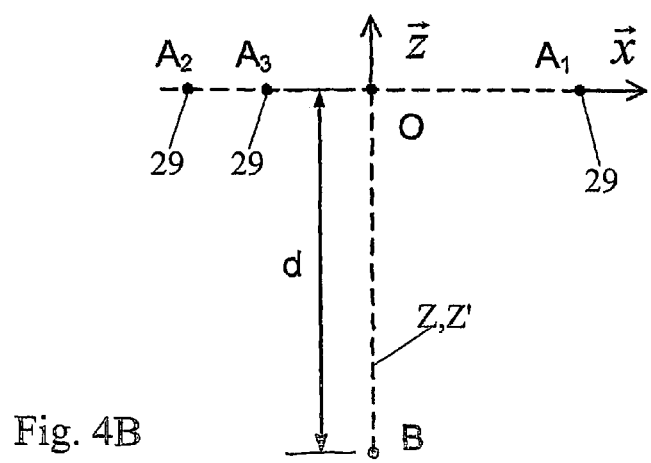

According to the example that is shown in FIG. 3 and diagrammatically repeated in FIGS. 4A and 4B, the force sensors 29 consist of unidirectional sensors that are oriented in the translational direction Z, are three in number, and are arranged in a plane that is orthogonal to said direction 2 and positioned symmetrically on a circle with radius r that is centered on the longitudinal axis Z' of the elongated body 2, whereby this arrangement of three sensors 29 thus allows the determination of two components of the reaction torque that is exerted on the elongated body 2.

In FIGS. 4A and 4B, the three sensors 29 are differentiated by the additional designations $A_1, A_2, A_3$. The point B designates, within the scope of a procedure for embedding the elongated body 2, the point of entry, whereby the latter is located at a distance d from the plane that is formed by the three sensors 29.

The component Z of the force F that is exerted by the body in which the elongated body 2 is introduced can be calculated from forces $m_1, m_2$ and $m_3$, measured by the three sensors as follows:

$$\vec{F} \cdot \vec{z} = Mg\vec{z}_0 \cdot \vec{z} - m_1 - m_2 - m_3.$$

In this formula, $\vec{z}$ indicates the axis of the elongated body 2, $\vec{z}_0$ indicates the direction of the gravity, M is the mass of the device 1 and $-g\vec{z}_0$ corresponds to the acceleration of the gravity.

Whereby the position and the orientation of the platform 3 remain unchanged during the movement of the elongated body, $Mg\vec{z}_0 \cdot \vec{z}$ constitutes a value that can be determined at the beginning of the procedure.

The specific arrangement of the unidirectional sensors 29 makes it possible to calculate two components of the torque that is exerted on the needle, expressed in terms of the point O:

$$\vec{M} \cdot \vec{x} = Mg\overrightarrow{OG} \wedge \vec{z}_0 \cdot \vec{x} - \frac{r}{2}m_2 - \frac{r\sqrt{3}}{2}m_3.$$

$$\vec{M} \cdot \vec{y} = Mg\overrightarrow{OG} \wedge \vec{z}_0 \cdot \vec{y} + rm_1 - \frac{r\sqrt{3}}{2}m_2 - \frac{r}{2}m_3.$$

In these two formulas, G indicates the mass center of the device 1.

Of course, the sensors 29 can also consist of multidirectional sensors that make it possible to provide measurements on the torque and the axial forces.

Figure 5A:
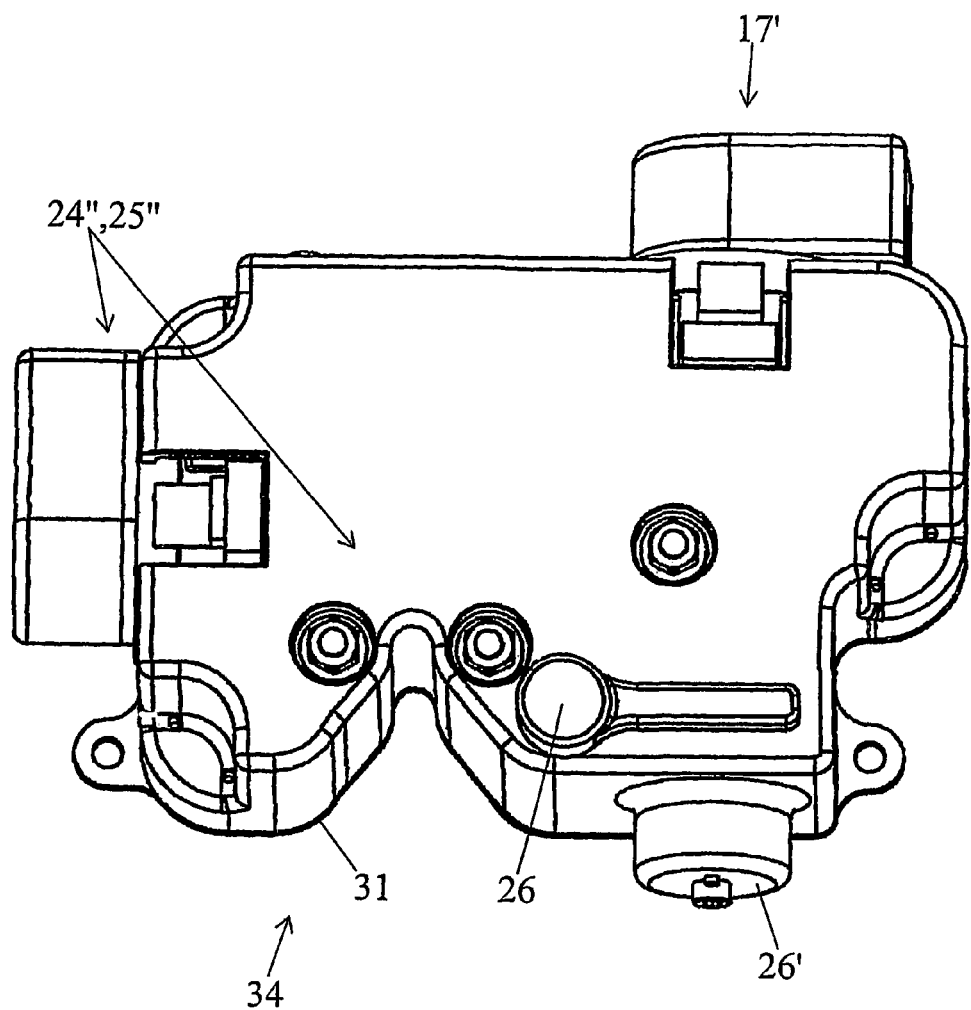
FIGS. 5A and 5B are perspective top views of the module combining the actuation mechanisms that are part of the device of FIG. 3, with the top closed and open, respectively.
Figure 5B:
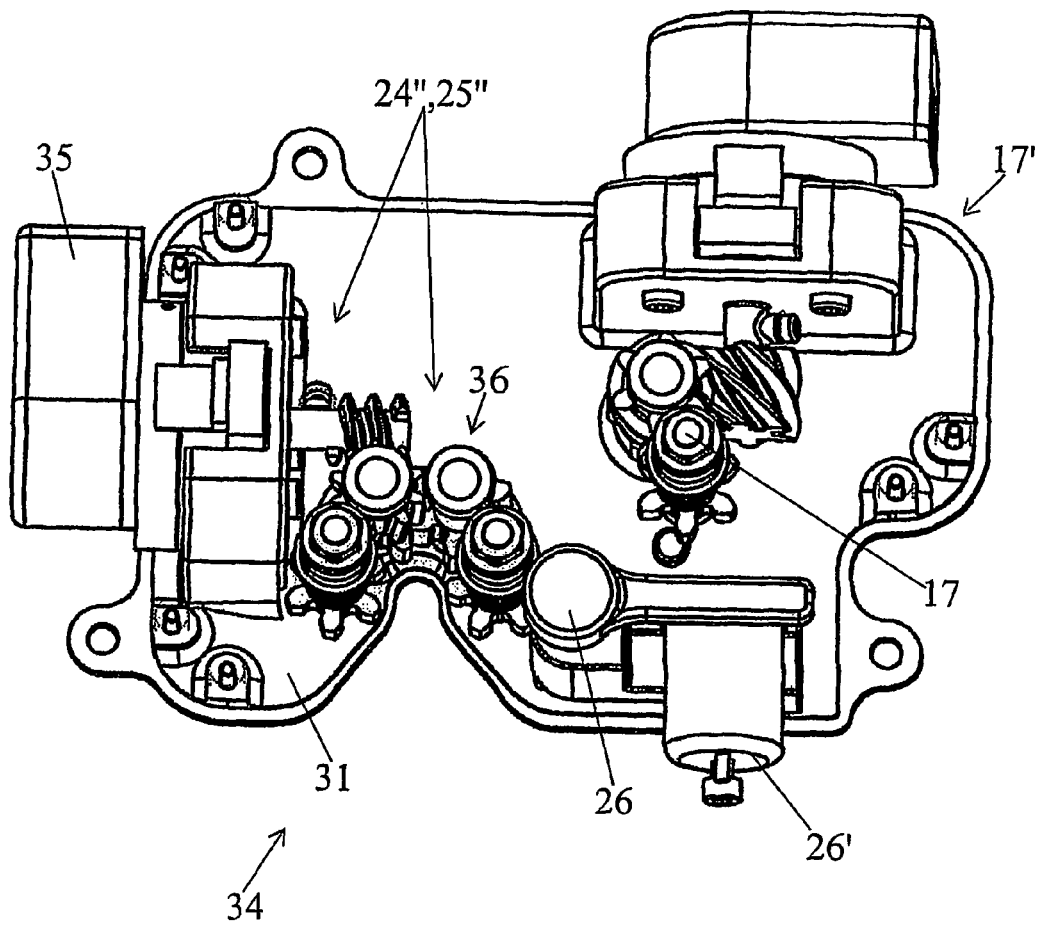
Figure 6:
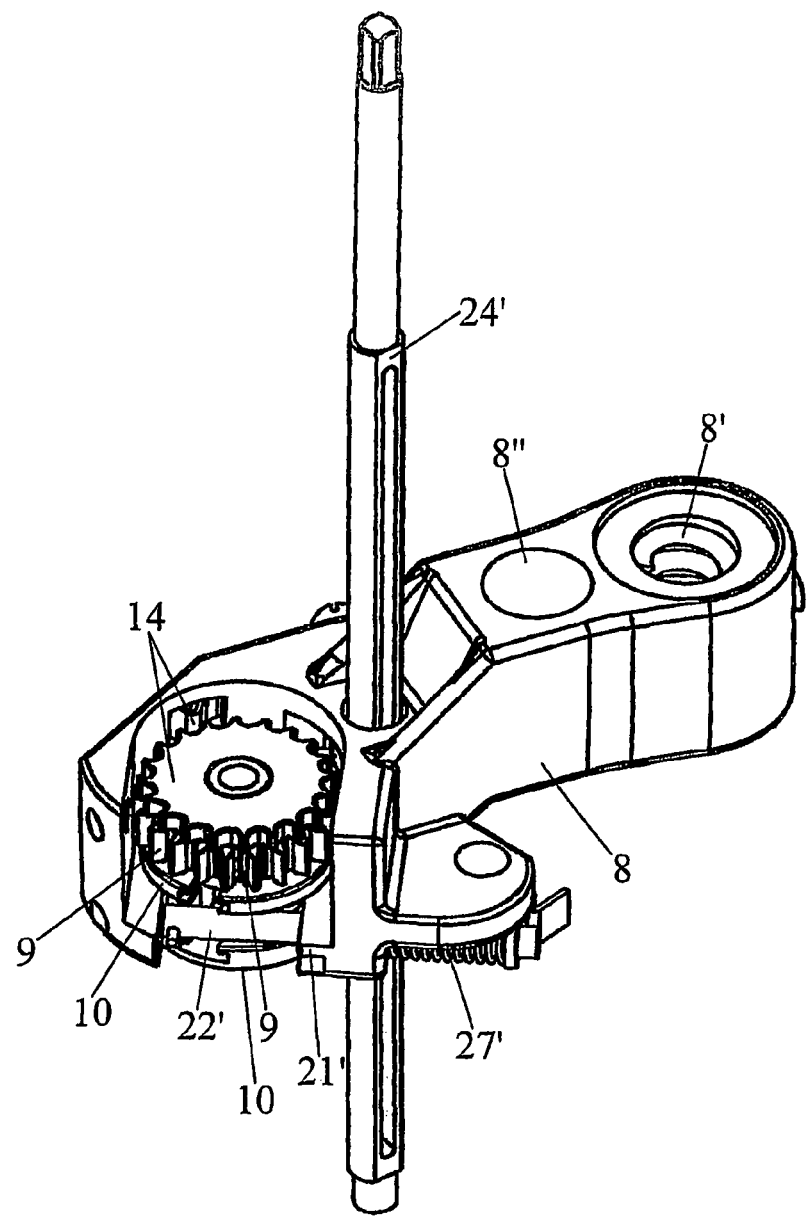
FIG. 6 is a detail perspective view of the cart that holds the first movable gripping part and that is part of the device of FIGS. 2 and 3.

For the purpose of contributing to a simple and compact assembly construction of the device 1, the actuators 24", 25" that drive the shafts 24', 25' are grouped on the support plate 31 that is connected to the platform 3 of the robotic device 4 opposite the support structure 15 that holds the first and second parts 5 and 6, whereby this support plate 31 also holds, if necessary, the actuating mechanism 26' of the control rod 26 that can move the locking pieces 22, 22' out of their locked position (FIGS. 5A and 5B).

The plate 31 can, for example, be connected to the upper plate 15" of the structure 15 by screws, which also pass through the plates 30 and the platform 3, by thus assembling these various elements between one another.

In accordance with an advantageous improvement of the invention, making it possible to simplify, to lighten and to reduce the cost of the device 1, it can be provided that the actuators 24", 25" of the shafts 24', 25' come in the form of a double actuator that integrates a single motor 35 with high torque and with a low rotation speed, for example of the piezoelectric type, and an arrangement 36 for transmission gears that transform the rotational movement of the outlet of said motor into two synchronous rotational movements in opposite directions, provided with two shafts 24' and 25'.

As FIGS. 5A and 5B also show, the support plate 31 also holds an actuator 17' for the threaded shaft 17, moving the cart 8—this, for example, in the form of a piezoelectric motor combined with a gear mechanism.

Figures 11, 11A, 11B:
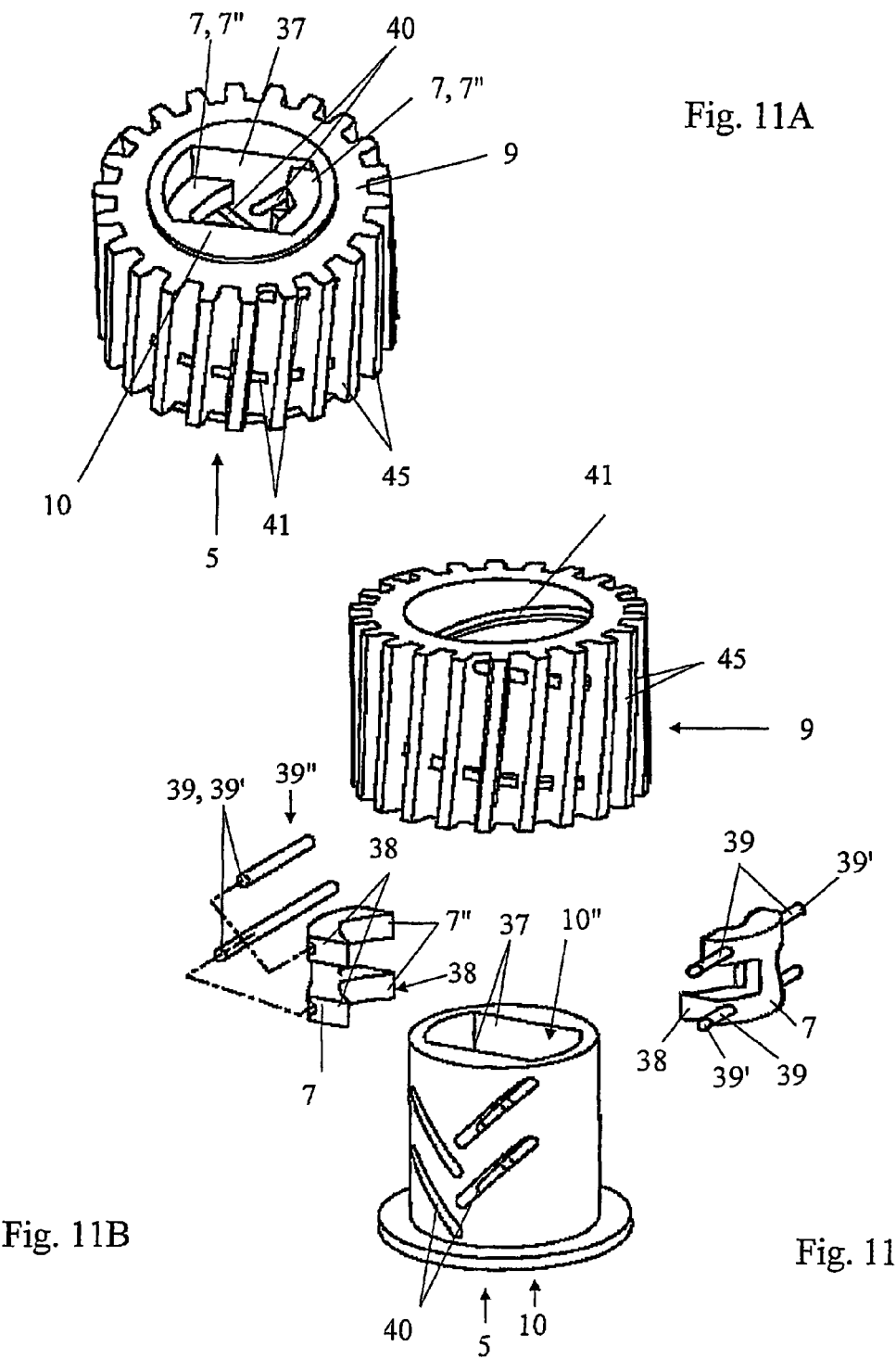
FIGS. 11A and 11B are perspective views, respectively in the assembled state and in the exploded state, of a first variant embodiment of a mandrel in connection with other embodiments of the device according to the invention.

In accordance with other embodiments of the mandrel 5, shown in FIGS. 11 and 12, the jaws 7 can be mounted guided in the tubular through passage 10" of the body 10, whereby said jaws 7 are provided with drive means 39 that are stressed, directly or indirectly, by the surrounding maneuvering ring 9, so as to be moved in translation according to Z or Z' during the rotation of this ring 9, by generating a simultaneous movement of mutual coming-together or moving-apart of said jaws 7 around the median axis of said passage 10" or an elongated body 2 that is mounted in said mandrel 5.

More specifically, the tightening means 7 can consist of two opposite and opposing jaws with mutually offset jaws 7" so as to interlock during their coming-together movement for the purpose of tightening. The tubular passage 10" then has two planar opposite faces 37 that form planar guide surfaces for said jaws 7, whereby the latter are also equipped with portions of lateral guide surfaces 38 that are suitable for sliding supported on said faces 37. Each of said jaws 7 is guided in an additional manner during their mutual coming-together and moving-apart movements to carry out travel in the direction Z or Z' simultaneously.

In accordance with a concrete embodiment of the guiding and entrainment of the jaws 7, each of said jaws 7 can be equipped with at least two drive and guide rods 39" that project laterally relative to its guide surface portions 38 and that each form a pair of opposite lugs or pins 39, whereby the latter are, on the one hand, mounted to slide in portions of grooves 40 that are made in the wall portions of the body 10 defining the planar opposite faces 37, coinciding two by two in the case of the two planar opposite faces 37 being superposed and located by coincident pairs in the planes or sloped non-planar surfaces relative to the longitudinal direction Z' of an elongated body 2 that is mounted in a tightened manner in the mandrel 5, and, on the other hand, at least for a pair of opposing pins or lugs 39 of each jaw 7, in direct or indirect drive connection with the maneuvering ring 9 at their ends 39' that go through portions of grooves 40 through which they pass, in view of their movement in the longitudinal direction Z' during a rotational movement of said maneuvering ring 9.

FIGS. 11 and 12 show the rods 39" in the disassembled state and in the assembled state (FIG. 11B) in through openings of the jaws 7, whereby the parts that exceed the latter form the pins or lugs 39.

By providing portions of grooves 40 that are inclined relative to the direction Z (i.e., not included in a plane that is perpendicular to this direction), it is possible to provide a release or radial travel of high amplitude for the jaws 7 because of a guided displacement combined simultaneously with a sliding displacement component in a plane that is perpendicular to the direction Z and a translational movement component according to this last direction.

The groove portions 40 have a rectilinear shape in FIGS. 11 and 12 and thereby produce a constant relationship between the two displacement components all along the travel of the jaws 7.

Nevertheless, other non-linear forms of groove portions 40 are possible, for example for using a higher tightening torque at the end of the coming-together travel of the two jaws 7.

Thanks in particular to this combined movement of jaws 7, combined with the particularly compact constitution of the mandrel 5, the ratio between the maximum inside opening of the mandrel 5, for a maximum separation from the jaws 7, and the outside diameter of the ring 9 can be obtained as more than 0.2, preferably at least 0.3.

Such a degree of opening makes it possible to ensure a total release of the body 2 in the open state (no more engagement of the jaws 7 with the body 2, but only a lateral hold with jarring in the tubular passage 10") and a large range of adaptation of the mandrel 5 to different diameters of the elongated bodies 2.

According to a first practical variant, emerging from FIGS. 11A and 11B, the body 10 can have a circular-cylindrical outside shape, adjusted in diameter to the inside diameter of the maneuvering ring 9, the ends 39' of the pins or lugs 39 that exceed groove portions 40 at the outside face of the body 10 that is guided to slide into the grooves 41 that are made at the inside face of the maneuvering ring 9 and formed by portions of curves each produced by the intersection between a determined regulated surface and the inside cylindrical surface of said ring 9, whereby the body 10 is locked in translation and is free in rotation in this surrounding ring 9.

Each jaw 7 then has at least two opposite pairs of lugs or pins 39, namely, a first longer pair that becomes engaged with the ring 9 and thus ensures the drive of said jaw 7, and at least a shorter second pair, which does not become engaged with the ring 9 and thus contributes solely to the guided displacement of said jaw 7 in cooperation with the first pair.

By way of example, the equation of curves will be used below, making it possible to generate the cutaways (grooves 41) in the ring 9 of the mandrel 5 of FIG. 11.

If a cylindrical reference is denoted as $(O, e_r, e_\theta, e_z)$,

If the inside cylindrical surface of the ring 9, the shaft $(O, e_z)$ and radius R are called C, and If the support straight line of the axis of one of the pins or lugs 39 is denoted as D, Then D, initially in the plane $(O, e_r, e_\theta)$ moves in a combined movement:

of translation following $(O, e_z)$ and in a radial direction $(O, e_4)$;

of rotation around $(O, e_z)$.

A groove 41 is obtained from intersecting curves of D and C.

The parametric equations of these curves, in the cylindrical reference $(O, e_r, e_\theta, e_z)$ are as follows:

For t varying from 0 to 1:

$$\begin{cases} r(t) = R \\ \theta(t) = \alpha(t) + \text{Arccos}\left(\frac{e(t)}{R}\right) \\ z(t) = f_1(t) \end{cases}$$

and $$\begin{cases} r(t) = R \\ \theta(t) = \alpha(t) - \text{Arccos}\left(\frac{e(t)}{R}\right) \\ z(t) = f_1(t) \end{cases}$$

For the particular embodiment proposed within the scope of the invention and illustrated in FIG. 11, a, e and $f_1$ are linear functions of time.

According to a second practical variant, emerging from FIGS. 12A and 12B, the body 10 can have a square or rectangular outside shape and can be mounted in the maneuvering ring 9 with insertion of an intermediate piece 42 that has a circular-cylindrical outside shape, adjusted in diameter to the inside diameter of the ring 9, and that has an inside shape that is complementary to the outside shape of the body 10, whereby this intermediate piece 42 is equipped, on the one hand, with grooves 43 coinciding by pairs, arranged by pairs in planes that are perpendicular to the median axis of the tubular passage 10" and that accommodate, with a guided sliding engagement, the ends 39' of the pins or lugs 39 that exceed portions of grooves 40 at the outside face of the body 10 and, on the other hand, at least two lugs 44 that project at its outside face and are guided to slide into grooves 41 that are essentially in the form of coils and are made at the inside face of the maneuvering ring 9, whereby the body 10 is locked in translation and free in rotation in this surrounding ring 9.

Advantageously, on its peripheral outside face, the maneuvering ring 9 has an inclined set of teeth 45 that is suitable for a functional engagement (interlinking) with an endless screw 46 for the purpose of its driving in rotation, a driving of said ring 9 beyond one degree of tightening determined from the elongated body 2 by the jaws 7, causing a rotation of the mandrel 5 and of the tightened body 2.

Thus, the body 2 can be driven and positioned in rotation in a controlled manner around its axis Z, whereby the mutual interlinking of the ring 5 and the screw 46 ensure a play-free kinematics.

According to another advantageous embodiment of the invention, emerging in particular from FIGS. 14 to 17, the mandrel 5 is secured, in a removable manner and with the capability of rotation, in a cart 8 that is mounted to slide in the translational direction Z in the elongated support structure 15 that is equipped with at least one suitable slide 47, whereby said structure is equipped with an upper plate 15" for its attachment to the platform 3 of the robotic device 4 and a lower plate 15' that comprises a guide opening or guide channel with play and with centering forming the second stationary part 6. Advantageously, a motorized assembly 48 for controlled movement of the cart 8 and a motorized assembly 49 for actuation of the maneuvering ring 9 are combined with the cart 8/support body 15 assembly by being mounted either on the platform 3 or on said support body 15.

The securing of the mandrel 5 in the cart 8, with the capability of rotation around the direction Z, can be obtained, for example, by providing in the cart 8 an annular housing of suitable shape with an introduction opening that can be shut off (by preserving a passage for the through body 2) by a removable cover 62 (also of annular shape).

Figure 16:
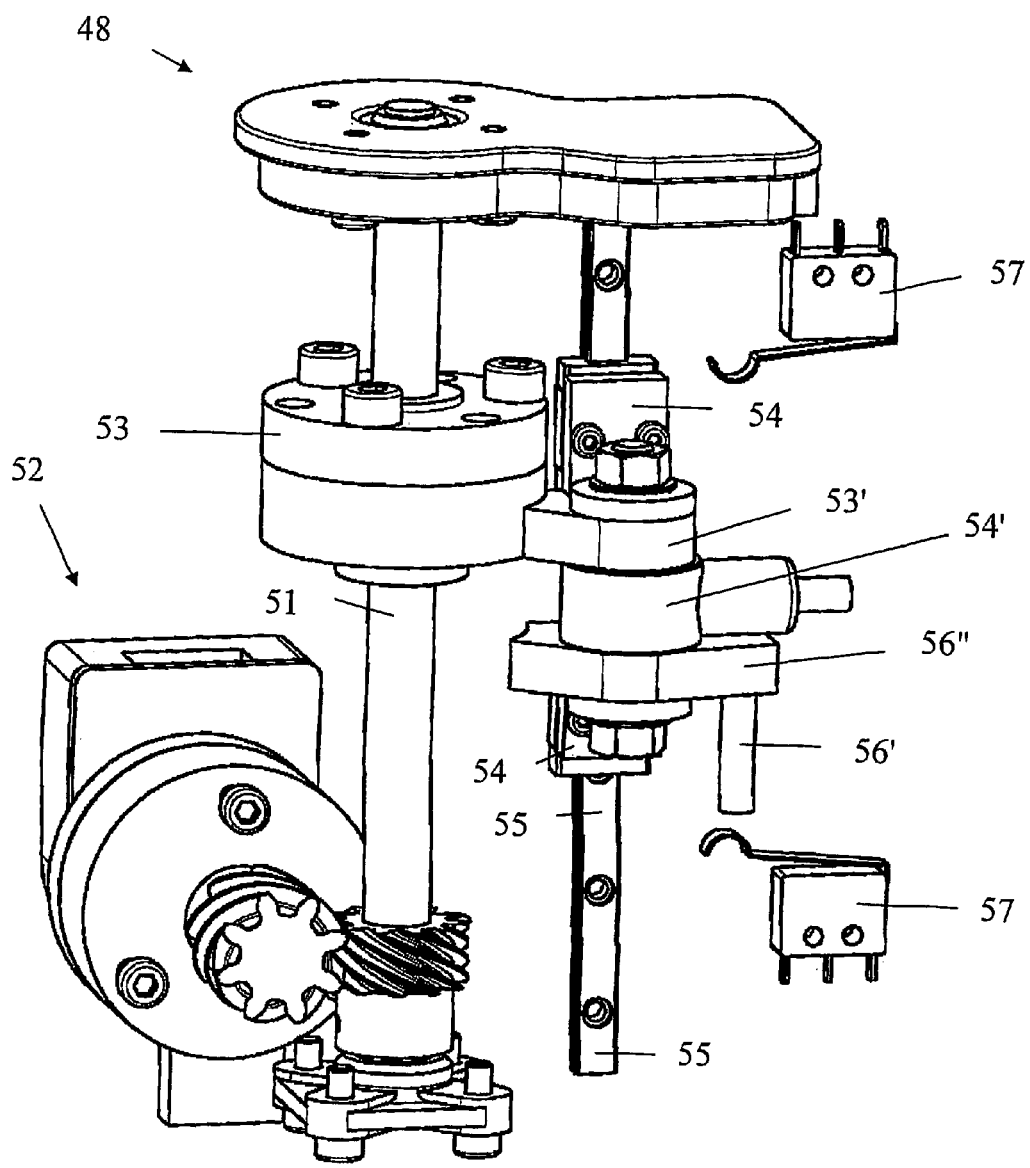
FIG. 16 is a perspective view, on a different scale and with the housing removed, of the motorized assembly for moving the cart that is part of the device of FIG. 15.
Figure 17:
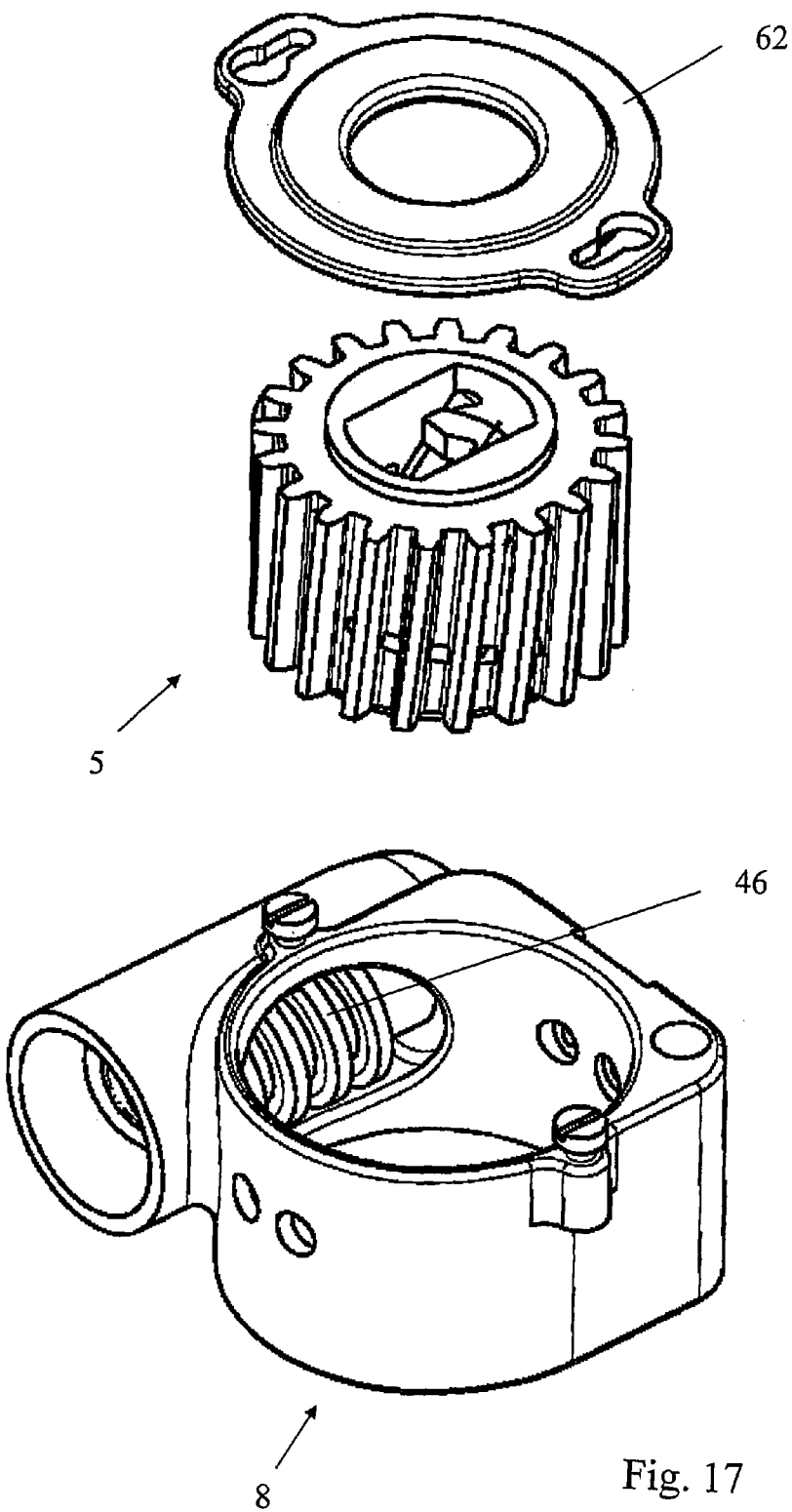
FIG. 17 is an exploded view and on a different scale from the cart that is part of the device of FIG. 14.

As FIGS. 15 and 16 show, the motorized driving assembly 48 can consist of, for example, a mother screw 51 that is driven in rotation by a motor unit 52 that optionally is combined with a position coder and that drives in translation a nut 53, whereby said nut 53 is connected rigidly to a cart or a pair of intermediate guide carts (54) that slide on a rail 55 that is parallel to the translational direction Z and to the slide 47. Said cart or carts 54 is (are) also connected rigidly to a site 56' for removable coupling of a connecting arm 56 that is integral with the cart 8. Whereby the points of attachment and connection of said nut 53 and of said coupling site 56' with the cart 54 or one of the carts 54 are connected to one another with insertion of a force sensor 54' that can measure the intensity of the mechanical actions in the direction Z, and said device 1 also comprises opposite ends-of-travel 57 that are mutually offset in the translational direction Z, and delimit the maximum travel of said intermediate cart(s) 54 and therefore of cart 8, said motorized assembly 48, with the exception of the ends-of-travel 57, is optionally mounted in a housing 60, formed by a single support with the platform 3 or accommodated, in an indexed way and with locking into position, in a receiving site 61 that is integral with the platform 3, by thus forming a removable autonomous module.

As FIGS. 14 and 15 show, the motorized actuation assembly 49 can consist of a motor unit 58 that drives, via a flexible drive shaft 59, an endless screw 46 that is integrated in the cart 8 that is engaged in driving with the peripheral maneuvering ring 9 of the mandrel 5 that is mounted in said cart 8, whereby said motor unit 58 is mounted in a housing that is formed by a single support with the platform 3 or accommodated in an indexed manner and with locking in position in a site for accommodating said platform 3.

The force sensor 54' performs a function that is similar to that of the three sensors 29, except for measuring only the stresses in the direction Z.

As FIG. 16 shows, the force sensor 54' can be sandwiched between a drive flange 53' that is integral with the nut 53 and a drive flange 56" that is integral with the coupling site 56', whereby the unit [53'/54'/56"] is mounted rigidly between the two carts 54 (FIG. 16).

The motor units 52 and 58 are preferably of the locking type in case of defect or absence of power supply and with a movement controlled by the sensor.

Of course, the invention that is described above, in connection with three different embodiments, can be used in a large number of applications and domains.

However, within the scope of a preferred application of the invention, the elongated body 2 consists of a needle for carrying out percutaneous medical procedures.

Such needles generally have a diameter that is less than one millimeter or several millimeters, and the device 1 will have a mandrel 5, and, if necessary, a mandrel 6, able to accommodate these different diameters and able to transmit a thrust force advantageously of at least 10 N, preferably about 15 N.

It will be noted that within the framework of such a medical application in particular, the results of the measurements of the sensors 29 can be displayed or reproduced in the form of resisting forces or opposing stresses at the level of a control part that is operated by the operator of the device 1.

This last variant thus makes it possible for a practitioner to comprehend the transitions of the passage of the needle 2 through the different anatomical structures.

Thus, as FIGS. 3, 13, 15 and 18 of the accompanying drawings show, the platform 3 of the robotic device 4 has an open cutaway 3', as well as optionally the upper plate 15" of the support structure 15 (itself perforated laterally), the intermediate mounting plate 50, the separator 30 that holds the force sensors 29 and the support plate 31 of the actuators 17', 24', 25', whereby the opening of this cutaway or these cutaways is oriented in the same direction as the openings 23, 23' of the mounting sites 16 and 19 of the first and second parts 5 and 6 and/or a lateral release of the support structure 15, so as to allow an installation and/or a lateral removal of said needle 2.

The cutaway 3', combined, if necessary, with the cutaway 32' of the plate 15", with the cutaway 33' of the separator 30 and with the cutaway 34' of the support plate 31, thus makes it possible to have a possibility of lateral engagement and disengagement (relative to the axial directions Z, Z') of the elongated body 2, for example in the form of a needle. When the parts 5 and 6 are released from their respective mounting sites 19 and 16, it thus is possible to quickly disengage and extract the body 2 from the device 1, without requiring manipulations or longitudinal extraction procedures that are complex and time-consuming. This is also possible when only the part 5 can be released.

As already indicated above and in connection with the first embodiment, the installation and the removal of the needle 2 will be carried out together with the mandrels 5 and 6 during the installation, whereby one of the latter is tightened and the other loosened.

In the embodiments of FIGS. 13 to 15, the mandrel 5 will also preferably be mounted tightened on the needle 2 before its mounting in the cart 8 or its introduction into the support body 15.

This invention also has as its object a system to assist in percutaneous medical procedures that are guided by medical imagery, comprising a robotic device for positioning and orientation of a platform, a device for controlled insertion and retraction of the needle and a device for piloting said devices based on preprogrammed parameters and instantaneous measurement results, such as measurements extracted from pre-operative medical images, measurements of stresses in the axial direction of the needle and/or torque stresses at said needle, or else indications or measurements of position that are provided by the above-mentioned robotic device and/or insertion device. This system is primarily characterized in that the device for inserting and retracting the needle consists of a device 1 as described above, in connection with any of its embodiments.

Figure 10:
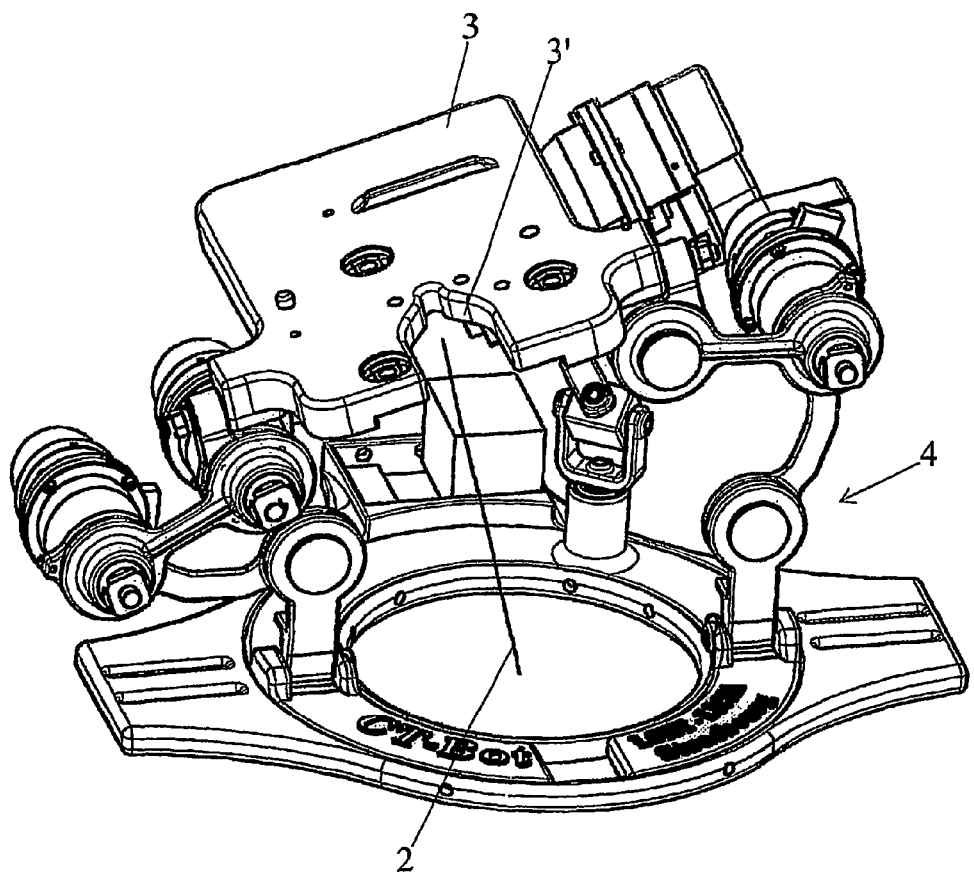
FIG. 10 is a perspective view of a robotic device for positioning and orientation that is able to support, at the level of its platform, a device according to the invention.
Figure 18:
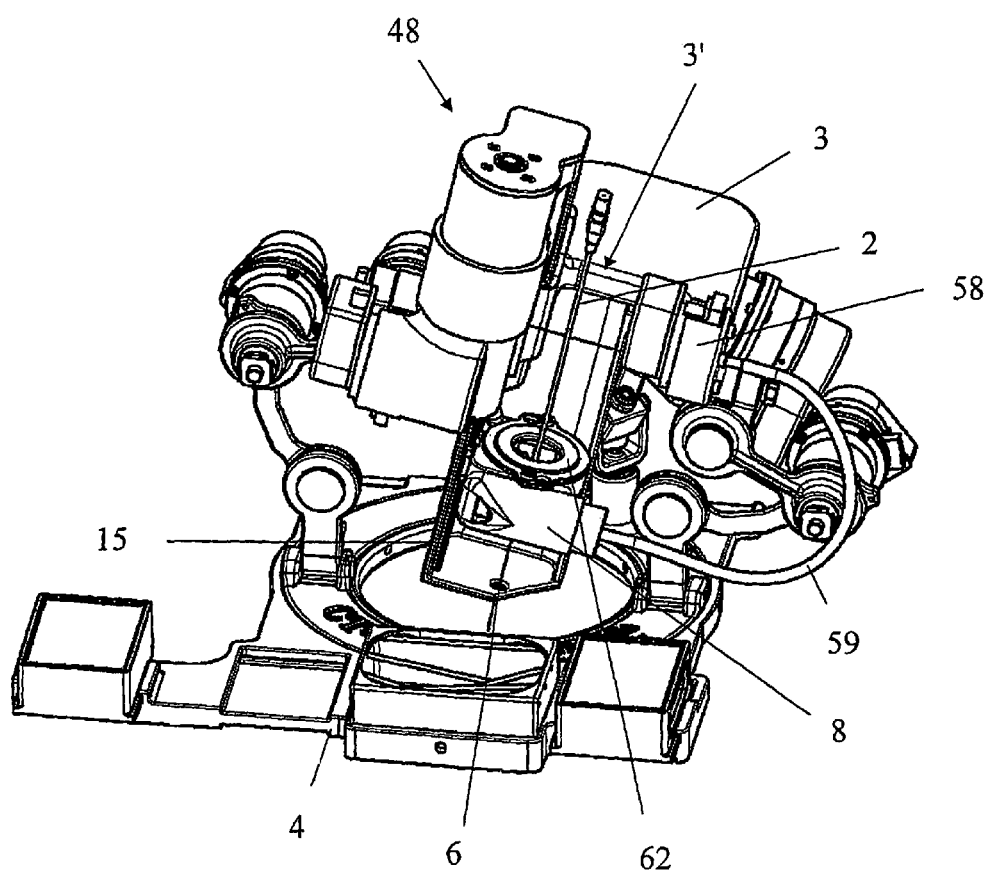
FIG. 18 is a perspective view of a robotic device such as the one of FIG. 10 that supports a device as shown in FIG. 14.

A possible construction of such a system can be obtained by combining the objects that are shown in FIGS. 3 and 10 (without the piloting device). Another possible design is shown in FIG. 18.

The robotic device 4 can in particular be of the type of the one that is described in:

"A Parallel 5 d of Positioner for Semi-Spherical Workspaces" (Positionneur à cinq degrés de liberté et à structure paralléle pour des volumes de travail semi-sphériques") by B. Maurin et al., Proceedings of the 2004 Asme Design Engineering Technical Conferences, DETC'04; or in the Patent Application PCT No. PCT/FR2005/002357 in the name of the applicants.

Advantageously, and as FIG. 3 of the accompanying drawings shows, in connection with a first embodiment, the device 1 for inserting and extracting the needle 2 can have a staged modular structure, with a first module 32 that contains the first and second parts 5 and 6 and the mechanical control means of the latter, whereby a second module 33 contains sensor means and a third module 34 contains the means for actuating the above-mentioned mechanical control means, whereby the second and third modules 33 and 34 are packed in a sterile package, together with a portion that is adjacent to at least the robotic device 4 for positioning and orientation, and whereby the first module 32 is produced, partially or totally, as a module of the expendable or single-use type.

Thus, with each new needle insertion 2, the replacement of the entire first module 32 or only a portion of the latter (for example, single mandrels 5 and 6) can be initiated based on in particular the cost of the module and/or its possibility of withstanding sterilization treatments.

In connection with the other embodiments of the invention, shown in FIGS. 13 to 18, it can be provided as a variant that the support body 15, if necessary with the cart 8 and optionally the hose 59, form(s) a module of the expendable or single-use type (just like the mandrel 5 and the needle 2), whereby the additional portions of the system (robotic system 4, platform 3, devices 48 and 49) are packed in a sterile package (before each use).

The support structure 15, the mandrel(s) 5 (and 6), and optionally some of the shafts or control rods can be produced from a polymer material that is resistant and easy to mold, if necessary reinforced by fibers.

As is evident from the preceding description, the device 1, in particular in the form of a device for inserting and extracting needles and based on its embodiment that is described above, has various safety properties.

Thus, from a kinematic standpoint, the gripping of the needle 2 and its movement are entirely decoupled and are produced via unidirectional transmission mechanisms. The control of the device 1 is thereby simplified, and the position of the point of the needle 2 is not influenced by its interaction with the environment.

In addition, the use of piezoelectric or ultrasonic motors also contributes to the safety of the device 1 in the case of a supply cutoff, since the configuration and the driving position of the needle 2 remain unchanged.

Finally, the mandrels that are connected to the needle can be extracted at any time during the phases of insertion and extraction, using the safety unlocking mechanism 22, 22', 26, 26'.

Regarding the requirements on sterility matters, it is possible to note that the device 1 can be subdivided into two parts, namely one active part that comprises the actuators and the sensors and that is connected to the platform 3 (this unit can be packed in a sterile package) and a passive or purely mechanical part that integrates the structure 15, the shafts and control rods and the mandrels (whereby this part is disposable and/or sterilizable).

Furthermore, it will be noted that the constituent materials of the various components of the device 1 are advantageously compatible with the type of medical imagery used, for example the scanner (in English, "CT scan").

Of course, the invention is not limited to the embodiment that is described and shown in the accompanying drawings. Modifications are possible, in particular from the standpoint of the composition of the various elements or by substitution of equivalent techniques, without thereby exceeding the scope of protection of the invention.

The invention claimed is:

1. A device for holding and for controlled translational movement, in a longitudinal direction, comprising:

a first gripping part (5) configured for gripping a needle (2), movable relative to a support (3) in a manner that is commanded and/or controlled in a translational direction (Z) with a predetermined maximum travel; and a second part (6) that is stationary relative to the support (3) and able to guide the needle (2) when the needle (2) is moved by the first movable gripping part (5) and, if necessary, to keep said needle (2) in position when the latter is not engaged with said first movable gripping part (5), the first and second parts (5 and 6) being aligned in the translational direction (Z) and whereby the first gripping part (5) can be moved alternatively between a proximal position of the second part (6) and a distant position of the device (1), wherein the first gripping part (5) comprises movable jaws (7), whereby the needle (2) is locked and the first gripping part (5) is a mandrel through which the needle (2) passes, whereby said mandrel (5) can be moved in rotation with the needle (2) around the translational direction (Z), and the jaws (7) are mounted, with a capability of guided sliding, in a body (10) with a tubular passage (10") that is designed to receive the needle (2), and the mandrel (5) presents in an open state a maximum opening of the jaws (7) and an opening degree to ensure total relaxation of the needle without lateral pulsation, such that movement of said jaws (7) is generated by a rotational movement of a rotary maneuvering ring (9) that surrounds the body (10), the needle being a needle for a percutaneous medical procedure, and the device is configured to be mounted on an adjustable support, a platform or an arm of a robotic device in a manner that is controlled in position and in orientation.

2. The device according to claim 1, wherein the mandrel (5) is mounted on or in a cart (8) that can be moved by motorized driving in two directions normal from the translational direction (Z) of said needle (2) by being guided in an elongated support structure (15) that is able to be assembled rigidly with the platform or the support (3) of a robotic device (4) for positioning and orientation, whereby said support structure (15) is advantageously shaped so as to allow lateral access to the needle (2) that is engaged in said support structure (15) and optionally an installation and an extraction at a lateral or radial slant from the needle (2), if necessary with the mandrel (5).

3. The device according to claim 2, wherein the second stationary part (6) is located at an end of the support body (15) with an elongated structure, which is distal relative to the platform or to the support (3) that holds said device (1), by being the body (10') that is connected to the support body (15) or formed by a portion of the support body (15).

4. The device according to claim 2, wherein the first moving part (5) and the second stationary part (6) are mounted, preferably in a removable manner, on a support structure (15) that can be assembled rigidly with the platform or the support (3) of a robotic device (4) for positioning and orientation, whereby the support structure (15) in the form of a chassis has a given extension in the translational movement direction (Z) of the needle (2), comprising a mounting site (16) for the second stationary part (6), positioned at the extreme end in the direction corresponding to a positive movement or embedding of said needle (2) in the translational direction (Z), and being equipped with means (17, 18) for guiding and for controlled movement of the first moving part (5) that is mounted, at a suitable corresponding mounting site (19), on or in a cart (8) that works with these means (17, 18).

5. The device according to claim 4, wherein the means for guiding and controlled movement of the first moving part (6) comprise, on the one hand, a threaded shaft (17) that forms a mother screw, and, on the other hand, at least one guide rail or rod (18), and wherein the cart (8) integrates a threaded perforation (8') that forms a nut and at least one bearing or guide shoe (8") that may or may not pass through and that works, in a sliding manner, with the guide rail or rod (18) or each guide rail or rod (18).

6. The device according to claim 5, wherein the driving of the maneuvering ring (9, 9') of each first and second parts in the form of a mandrel (5, 6) is carried out via a gear (24, 25) that engages with said maneuvering ring (9, 9') and is integral in rotation with a rod or a shaft (24', 25') that is driven in rotation by a corresponding, respective actuator (24", 25"), wherein the gear (25) that engages with the maneuvering ring (9') of the stationary, second part mandrel (6) is made integral rigidly at the end of a corresponding drive shaft (25') and wherein the gear (24) that engages with the maneuvering ring (9) of the moving, first gripping part mandrel (5) is integral in rotation and free in translation relative to a corresponding drive shaft (24').

7. The device according to claim 6, wherein the shafts (24' and 25') have free ends, on the side of the actuators (24", 25") being tapered or pointed, such that they are able to pierce a wall of a sterile package.

8. The device according to claim 6, wherein the chassis that forms a support structure (15) comprises a lower plate (15') that contains the mounting site at the extreme end (16) for the second part (6) and an upper plate (15") for attachment to the support (3) of a robotic device (4) for operation and orientation, whereby said upper plate (15") is equipped with quick assembly means (28), such as, for example, latches, able to become engaged with said support (3) or with a piece that is integral with the latter in the mounted state of said chassis (15), and wherein the means (17, 18) for guiding and controlled movement, as well as, the shafts (24', 25') extend and are mounted between these two plates (15' and 15"), whose mutual spacing essentially determines the travel of the first moving part (5).

9. The device according to claim 8, further comprising force sensors (29) that measure the intensity of the thrust exerted on the needle (2) in the translational direction (Z), and, if necessary, the torque or certain components at least of the torque that is exerted on this needle (2).

10. The device according to claim 9, wherein the force sensors (29) are arranged between the upper plate (15") of the support structure (15) and the support (3) of the robotic device (4) by preferably being mounted on a separator (30) that is sandwiched between said upper plate (15") and said platform (3).

11. The device according to claim 9, wherein the force sensors (29) consist of unidirectional sensors that are oriented in the translational direction (Z), are three in number and are arranged in a plane that is orthogonal to said direction (2) and positioned symmetrically on a circle with radius (r) that is centered on the longitudinal axis (Z') of the needle (2), whereby this arrangement of three sensors (29) thus allows the determination of two components of the reaction torque that is exerted on the needle (2).

12. The device according to claim 6, wherein the actuators (24", 25") that drive the shafts (24', 25') are grouped on a support plate (31) that is connected to the support (3) of the robotic device (4) opposite the support structure (15) that holds the first and second parts (5 and 6).

13. The device according to claim 12, wherein the actuators (24", 25") of the shafts (24', 25') come in the form of a double actuator that integrates a single motor (35) with high torque and with a low rotation speed, for example of the piezoelectric type, and an arrangement (36) for transmission gears that transform the rotational movement of the outlet of said motor into two synchronous rotational movements in opposite directions, provided with two shafts (24' and 25').

14. The device according to claim 12, wherein the support plate (31) also holds an actuator (17') for the threaded shaft (17), moving the cart (8), this, for example, in the form of a piezoelectric motor combined with a gear mechanism.

15. The device according to claim 4, wherein the first and second parts (5 and 6) that come in the form of mandrels are accommodated in a removable manner and with the capability of rotation in their respective essentially U-shaped mounting sites (16 and 19), wherein the bodies (10, 10') of the mandrels (5, 6) that are generally circular-cylindrical in shape have an outside circumferential groove (20, 20'), and the mounting sites (16 and 19) each have a rib (21, 21') that can work with the groove (20, 20') of the corresponding body (10, 10') of mandrel (5, 6), over a portion of their circumferential extension, for the purpose of the retention of said body (10, 10'), and wherein said mounting sites (16, 19) are open laterally to allow the installation and removal of said mandrels (5, 6), whereby the latter are locked in the mounted state in their respective sites (16, 19) by moving locking pieces (22, 22'), preferably stressed elastically in the locking position of said mandrels (5, 6), whereby these locking pieces (22, 22') become engaged in the outside grooves (20, 20') of the body (10, 10') of the mandrels (5, 6) respectively in question in the continuity of the ribs (21, 21') and by closing the lateral openings (23, 23') of the respective mounting sites (16, 19).

16. The device according to claim 15, wherein the first and second parts (5 and 6) are mounted in their mounting sites (19 and 16) respectively against an elastic stressing, whereby the latter ejects said parts (5 and 6) beyond said sites (19 and 16) when the locking pieces (22, 22'), preferably controlled simultaneously, release the corresponding lateral openings (23 and 23').

17. The device according to claim 15, further comprising a pivoting or sliding control rod or pole (26) that is connected in driving with the locking pieces (22, 22') for the purpose of their travel beyond their locking position against elastic stressing forces, for example provided by compression springs (27, 27'), whereby this control rod (26) is integral in driving an actuating mechanism (26'), in particular a safety mechanism that causes unlocking by default.

18. The device according to claim 15, wherein the support (3) of the robotic device (4) has an open cutaway (3'), as well as optionally the upper plate (15") of the support structure (15), the separator (30) that holds the force sensors (29) and the support plate (31) of the actuators (17', 24', 25'), whereby the opening of this cutaway or these cutaways is oriented in the same direction as the openings (23, 23') of the mounting sites (16 and 19) of the first and second parts (5 and 6), and/or as a lateral release of the structure (15), so as to allow an installation and/or a lateral removal of said needle (2).

19. The device according to claim 2, wherein the cart (8) that holds the gripping part (5) is connected in a removable manner to said device (1) by being able to be moved in particular into an end sliding position at the level of which it disengages from said device (1).

20. The device according to claim 2, wherein the mandrel (5) is secured, in a removable manner and with the capability of rotation, in a cart (8) that is mounted to slide in the translational direction (Z) in the elongated support structure (15) that is equipped with at least one suitable slide (47), whereby said structure (15) is equipped with an upper plate (15") for its attachment to the support (3) of the robotic device (4) and a lower plate (15') that comprises a guide opening or guide channel forming the second stationary part (6), and wherein a first motorized assembly (48) for controlled movement of the cart (8) and a second motorized assembly (49) for actuation of the maneuvering ring (9) are combined with the cart (8)/support body (15) assembly by being mounted either on the support (3) or on said support structure (15).

21. The device according to claim 20, wherein the first motorized assembly (48) is formed from a mother screw (51) that is driven in rotation by a motor unit (52) that optionally is combined with a position coder and that drives in translation a nut (53), whereby said nut (53) is connected rigidly to at least one intermediate guide cart (54) that slides on a rail (55) that is parallel to the translational direction (Z) and to the slide (47), wherein said at least one cart (54) is connected rigidly to a site (56') for removable coupling of a connecting bar (56) that is integral with the cart (8), wherein the points of attachment and connection of said nut (53) and of said coupling site (56') with the at least one cart (54) is connected to a next cart with insertion of a force sensor (54') that can measure the intensity of the mechanical actions in the direction (Z), and wherein said device comprises opposite ends-of-travel (57) that are mutually offset in the translational direction (Z) and that delimit the maximum travel of said intermediate cart or carts (54) and therefore of cart (8), whereby said first motorized assembly (48), with the exception of the ends-of-travel (57), is optionally mounted in a housing (60), formed by a single support with the support (3) or accommodated, in an indexed way and with locking into position, in a receiving site (61) that is integral with the support (3), by thus forming a removable autonomous module.

22. The device according to claim 20, wherein the second motorized assembly (49) is formed from a motor unit (58) that drives, via a flexible drive shaft (59), an endless screw (46) that is integrated in the cart (8) and is engaged in driving with the peripheral maneuvering ring (9) of the mandrel (5) that is mounted in said cart (8), whereby said motor unit (58) is mounted in a housing that is formed by a single support with the support (3) or accommodated in an indexed manner and with locking in position in a site for accommodating said support (3).

23. The device according to claim 2, wherein the cart (8) has an annular shape adapted to receive the mandrel (5) removably and rotatably, and a housing is provided with an opening configured for introduction of the mandrel (5), which is closed by a removable cover (62).

24. A system to assist in percutaneous medical procedures that are guided by medical imagery, comprising a robotic device for positioning and orienting a platform, a device for controlled insertion and retraction of a needle, and a device for piloting said devices based on preprogrammed parameters and results of instantaneous measurements, such as measurements extracted from preoperative medical images, measurements of stresses in the axial direction of the needle and/or torque stresses at said needle, or else indications or measurements of position that are provided by the above-mentioned robotic device and/or insertion device, wherein the device for insertion and retraction of the needle is the device (1) according to claim 2.

25. The system according to claim 24, wherein the device (1) for inserting and extracting the needle (2) has a staged modular structure, with a first module (32) that contains the first and second parts (5 and 6) and means for mechanical control means of the first and second parts (5 and 6), whereby a second module (33) contains sensor means, and a third module (34) contains the means for actuating the above-mentioned mechanical control means, whereby the second and third modules (33 and 34) are packed in a sterile package, together with a portion that is adjacent to at least the robotic device (4) for positioning and orientation, and whereby the first module (32) is produced, partially or totally, as a module that is expendable or single-use.

26. The system according to claim 24, wherein the support body (15), the cart (8) and a hose (59), form a module that is expendable or single-use, whereby the additional portion of the system is packed in a sterile package.

27. The device according to claim 1, wherein the mandrel (5) is accommodated directly in a support body (15) that is elongated with the capability of guided sliding in the translational direction (Z) of the needle (2) and with the capability of rotation around an axis, whereby said support body (15) forms a slide for said moving the mandrel (5), whose travel results directly from the manual action of an operator, whereby said support body (15) is advantageously shaped so as to allow lateral access to the needle (2) that is engaged in said support body (15) and optionally an installation and an extraction at a lateral or radial slant from the needle (2).

28. The device according to claim 1, wherein the second stationary part (6) consists of an adjusted guide bearing of the needle (2), whereby the friction between the latter and said bearing is at least enough to ensure that said needle (2) is held against gravity.

29. The device according to claim 1, wherein the second stationary part (6) consists of an opening or a guide channel with play of the needle (2), designed to limit the radial jarring or the angular slope of the needle (2) relative to the translational direction (Z) and to hold said needle (2) essentially in a coaxial arrangement with said translational direction (Z), in cooperation with the mandrel (5) that forms a moving gripping and driving part.

30. The device according to claim 1, wherein the second stationary part (6) performs a controlled gripping function of the needle (2) and consists of a second mandrel through which the needle (2) extends, whereby this second mandrel (6) has a structure, a mode of operation and constituent elements that are identical to those of the first gripping part mandrel (5), namely in particular a maneuvering ring (9'), jaws (7'), and a body (10') with a tubular passage (10").

31. The device according to claim 8, wherein the first gripping part mandrel (5) or each of the first gripping part and second mandrels (5, 6) essentially consists of a body (10, 10') with a tubular through passage (10"), open laterally for allowing the passage of at least two, preferably three, jaws (7, 7') and equipped with guide means (11, 11') of said jaws (7, 7') in a radial direction relative to the tubular passage of the body (10, 10') in question, wherein said jaws (7, 7') are distributed uniformly around said passage (10") and can be moved between a so-called tightening position in which they extend partially into the corresponding passage (10") and a position in which they totally release said passage (10"), and wherein said jaws (7, 7') comprise rib/groove segments (12) that can be engaged and that can circulate in a groove/rib (13) in a spiral portion that is made in a lateral face of a toothed maneuvering ring gear (9, 9') that is mounted with the capability of rotation on a portion with a tubular external shape (10''') of the body (10, 10') of the mandrel in question (5, 6), whereby a rotation of said ring (9 or 9') entrains a simultaneous or identical radial slide of the jaws (7 or 7').

32. The device according to claim 31, wherein the first gripping part and second mandrels (5, 6) is mounted with the capability of rotation around the longitudinal axis (Z') of the needle (2) that passes through it, if necessary, together with the latter, and wherein with each mandrel (5, 6), there is associated a pawl mechanism (14, 14') that locks the body (10, 10') of said mandrel (5, 6) in question against rotation in the direction of loosening and that allows a gradual rotation of said mandrel (5, 6), in the direction of tightening, when the latter is thoroughly tightened around the needle (2), and wherein an additional tightening torque, having an intensity that is greater than a determined value defined by the pawl mechanism (14, 14') in question is applied at the corresponding toothed maneuvering ring (9, 9').

33. The device according to claim 1, wherein the jaws (7) that tighten the mandrel (5) are mounted in the tubular through passage (10") of the body (10), whereby said jaws (7) are equipped with means for driving (39) that are stressed, directly or indirectly, by the surrounding maneuvering part (9), which forms a ring so as to be moved in translation along the translational direction (z) or a longitudinal axis (z') during the rotation of the ring (9) by generating a simultaneous movement of mutual coming-together or moving-apart of said jaws (7) around a median axis of said tubular passage (10") or the needle (2) that is mounted in said mandrel (5).

34. The device according to claim 33, wherein the jaws (7) are formed from two opposite and opposing jaws with mutually offset jaws (7") so as to interlock during their coming-together movement for the purpose of tightening, wherein the tubular passage (10") has two planar opposite faces (37) that form planar guide surfaces for said jaws (7), whereby the jaws (7) are also equipped with portions of lateral guide surfaces (38) that are suitable for sliding supported on said faces (37) and wherein each of said jaws (7) is guided in an additional manner during their mutual coming-together and moving-apart movements to carry out travel in the translational direction (z) or the longitudinal axis (z') simultaneously.

35. The device according to claim 34, wherein each of said jaws (7) are equipped with at least two drive and guide rods (39"') that project laterally relative to its guide surface portions (38) and wherein each form a pair of opposite lugs or pins (39), and the lugs or pins (39) mounted to slide in portions of grooves (40) that are made in the wall portions of the body (10) defining the planar opposite faces (37), coinciding two by two in the case of the two planar opposite faces (37) being superposed and located by coincident pairs in planes or sloped non-planar surfaces relative to the longitudinal direction (Z') of the needle (2) that is mounted in a tightened manner in the mandrel (5), and at least one pair of opposing pins or lugs (39) of each jaw (7), in direct or indirect drive connection with the maneuvering ring (9) at their ends (39') go through portions of grooves (40) through which they pass, in view of their movement in the longitudinal direction (Z') during a rotational movement of said maneuvering ring (9).

36. The device according to claim 35, wherein the body (10) has a circular-cylindrical outside shape, adjusted in diameter to the inside diameter of the maneuvering ring (9), the ends (39') of the pins or lugs (39) that exceed groove portions (40) at the outside face of the body (10) that is guided to slide into the grooves (41) that are made at the inside face of the maneuvering ring (9) and formed by portions of curves each produced by the intersection between a regulated surface and an inside cylindrical surface of said ring (9), whereby the body (10) is locked in translation and is free in rotation in this surrounding maneuvering ring (9).

37. The device according to claim 35, wherein the body (10) has a square or rectangular outside shape and is mounted in the maneuvering ring (9) with insertion of an intermediate piece (42) that has a circular-cylindrical outside shape, adjusted in diameter to the inside diameter of the maneuvering ring (9), and that has an inside shape that is complementary to the outside shape of the body (10), whereby this intermediate piece (42) is equipped, on the one hand, with grooves (43) coinciding by pairs, arranged by pairs in planes that are perpendicular to the median axis of the tubular passage (10") and that accommodate, with a guided sliding engagement, the ends (39') of the pins or lugs (39) that exceed portions of grooves (40) at the outside face of the body (10) and, on the other hand, at least two lugs (44) that project at its outside face and are guided to slide into grooves (41) that are essentially in the form of coil portions and are made at the inside face of the maneuvering ring (9), whereby the body (10) is locked in translation and free in rotation in this surrounding ring (9).

38. The device according to claim 34, wherein a ratio between a maximum inside opening of the mandrel (5), for a maximum separation from the jaws (7), and an outside diameter of the ring (9) is more than 0.2.

39. The device according to claim 33, wherein on its peripheral outside face, the maneuvering ring (9) has an inclined set of teeth (45) that is suitable for a functional engagement with an endless screw (46) for the purpose of its driving in rotation, a driving of said maneuvering ring (9) beyond one degree of tightening determined from the elongated body (2) by the jaws (7), causing a rotation of the mandrel (5) and of the tightened body (2).

* * * * *